(12) United States Patent
Bergen et al.

(10) Patent No.: US 11,488,716 B2
(45) Date of Patent: Nov. 1, 2022

(54) METHOD FOR CONFIGURING MULTIPLE MACHINE LEARNING CLASSIFIERS

(71) Applicant: Ferrum Health, Inc., San Francisco, CA (US)

(72) Inventors: Leon Bergen, San Diego, CA (US); Pelu S Tran, San Francisco, CA (US); Kenneth Ko, Santa Clara, CA (US)

(73) Assignee: Ferrum Health, Inc., San Francisco, CA (US)

( * ) Notice: Subject to any disclaimer, the term of this patent is extended or adjusted under 35 U.S.C. 154(b) by 535 days.

(21) Appl. No.: 16/592,708

(22) Filed: Oct. 3, 2019

(65) Prior Publication Data
US 2020/0111572 A1    Apr. 9, 2020

Related U.S. Application Data

(63) Continuation-in-part of application No. 16/155,804, filed on Oct. 9, 2018, now Pat. No. 11,227,689.

(51) Int. Cl.
| G06F 15/177 | (2006.01) |
| G16H 50/20 | (2018.01) |
| G16H 10/60 | (2018.01) |
| G06N 5/04 | (2006.01) |
| G06N 20/00 | (2019.01) |
| G16H 15/00 | (2018.01) |

(52) U.S. Cl.
CPC ............. *G16H 50/20* (2018.01); *G06N 5/045* (2013.01); *G06N 20/00* (2019.01); *G16H 10/60* (2018.01); *G16H 15/00* (2018.01)

(58) Field of Classification Search
None
See application file for complete search history.

(56) References Cited

U.S. PATENT DOCUMENTS

| 10,874,355 | B2* | 12/2020 | Vaughan | G06N 20/10 |
| 2008/0103849 | A1 | 5/2008 | Forman et al. | |
| 2009/0281981 | A1 | 11/2009 | Chen et al. | |
| 2016/0129282 | A1 | 5/2016 | Yin et al. | |
| 2016/0350919 | A1 | 12/2016 | Steigauf et al. | |
| 2016/0364862 | A1 | 12/2016 | Reicher et al. | |
| 2017/0220735 | A1* | 8/2017 | Duenwald | C12Q 1/6869 |
| 2018/0060535 | A1 | 3/2018 | Reicher | |
| 2018/0365581 | A1* | 12/2018 | Vasseur | G06N 7/005 |
| 2019/0277913 | A1* | 9/2019 | Honda | G01R 31/2894 |

(Continued)

OTHER PUBLICATIONS

Final Office Action dated, dated Sep. 15, 2021, for corresponding application, U.S. Appl. No. 16/155,804, filed Oct. 9, 2018.

(Continued)

*Primary Examiner* — Phuoc H Nguyen
(74) *Attorney, Agent, or Firm* — Fountainhead Law Group P.C.

(57) ABSTRACT

Configuring a multi-classification system having multiple component classifiers includes storing of data records that represent different levels of performance of the system. The component classifiers are configured with corresponding decision threshold values contained in a selected one of the data records. Performance of the multi-classification system subsequent to configuring the component classifiers is approximated by the performance level associated with the selected data record.

27 Claims, 14 Drawing Sheets

(56) References Cited

U.S. PATENT DOCUMENTS

2020/0111024 A1  4/2020  Bergen et al.
2020/0111570 A1  4/2020  Tran et al.

OTHER PUBLICATIONS

International Search Report, Application No. PCT/US19/55065, dated Mar. 12, 2020, 8 pages.
Non Final Office Action dated, dated Jul. 6, 2020, for corresponding application, U.S. Appl. No. 16/155,804, filed Oct. 9, 2018.
Extended European Search Report dated Jun. 7, 2022, European Patent Office, EP Application No. 19871096.4, 8 pages.

* cited by examiner

METHOD FOR CONFIGURING MULTIPLE MACHINE LEARNING CLASSIFIERS

CROSS REFERENCE TO RELATED APPLICATIONS

This application is a continuation-in-part application and, pursuant to 35 U.S.C. § 120, is entitled to and claims the benefit of earlier filed application U.S. application Ser. No. 16/155,804, filed Oct. 9, 2018, the content of which is incorporated herein by reference in its entirety for all purposes.

This application is related to concurrently filed application U.S. application Ser. No. 16/592,759, filed Oct. 3, 2019, entitled "METHOD FOR COMPUTING PERFORMANCE IN MULTIPLE MACHINE LEARNING CLASSIFIERS," the content of which is incorporated herein by reference in its entirety for all purposes.

BACKGROUND

The present disclosure relates to medical diagnostics and in particular, to systems and methods for verifying medical diagnoses.

Accurate diagnosis of a health condition can be a life or death situation for a patient. Typically, tests are conducted by hospitals and the results are analyzed by doctors. The doctor's analysis it typically memorialized in a doctor's report, which is manually created by the doctor, assistants, and/or other medical professionals.

However, human error can occur, and diagnoses are not always correct. An incorrect diagnosis may have dramatic impact on the life of a patient. It would be advantageous to have a diagnosis system that worked together with doctors to help verify the doctor's medical analysis.

SUMMARY

Embodiments in accordance with the present disclosure are directed to configuring a system comprising a plurality of component classifiers. A plurality of data records that represent measures of performance of the system are stored. Each data record is associated with a performance level of the system. Each data record includes: (1) a plurality of decision thresholds for the plurality of component classifiers; (2) a system true-positive rate (TPR) representative of a TPR that characterizes the system when the plurality of component classifiers comprising the system are configured with the plurality of decision thresholds in the data record; and (3) a system false-positive rate (FPR) representative of an FPR that characterizes the system when the plurality of component classifiers comprising the system are configured with the plurality of decision thresholds in the data record. The performance level that is associated with the data record is based on the system TPR and the system FPR. The plurality of component classifiers comprising the system are configured with the plurality of decision thresholds in a data record selected from among the plurality of data records; the data record being selected based on the performance levels of the data records. When the system is operated according to the configured plurality of component classifiers, the system operates at a performance level that is approximated by the performance level associated with the selected data record.

In some embodiments, the plurality of data records can be presented to a user. Information can be received from the user indicative of one of the plurality of data records as the selected data record.

In some embodiments, the system TPR and the system FPR in each data record are determined based at least on component TPRs and component FPRs associated with the plurality of component classifiers comprising the system configured with the plurality of decision thresholds in said each data record. In some embodiments, the component TPR and the component FPR of each component classifier in the plurality of component classifiers is representative of a respective TPR and FPR that characterizes said each component classifier when said each component classifier is configured with a corresponding decision threshold from the plurality of decision thresholds in said each data record.

In some embodiments, the plurality of data records is a subset of a plurality of candidate data records that is greater in number than the plurality of data records.

In some embodiments, the plurality of data records represents a Pareto frontier among a plurality of candidate data records that is greater in number than the plurality of data records.

BRIEF DESCRIPTION OF THE DRAWINGS

With respect to the discussion to follow and in particular to the drawings, it is stressed that the particulars shown represent examples for purposes of illustrative discussion and are presented in the cause of providing a description of principles and conceptual aspects of the present disclosure. In this regard, no attempt is made to show implementation details beyond what is needed for a fundamental understanding of the present disclosure. The discussion to follow, in conjunction with the drawings, makes apparent to those of skill in the art how embodiments in accordance with the present disclosure may be practiced. Similar or same reference numbers may be used to identify or otherwise refer to similar or same elements in the various drawings and supporting descriptions. In the accompanying drawings.

DETAILED DESCRIPTION

In the following description, for purposes of explanation, numerous examples and specific details are set forth in order to provide a thorough understanding of the present disclosure. It will be evident, however, to one skilled in the art that the present disclosure as expressed in the claims may include some or all of the features in these examples, alone or in combination with other features described below, and may further include modifications and equivalents of the features and concepts described herein.

In the following description, for purposes of explanation, numerous examples and specific details are set forth in order to provide a thorough understanding of the present disclosure. Such examples and details are not to be construed as unduly limiting the elements of the claims or the claimed subject matter as a whole. It will be evident to one skilled in the art, based on the language of the different claims, that the claimed subject matter may include some or all of the features in these examples, alone or in combination, and may further include modifications and equivalents of the features and techniques described herein.

Figure 1A:
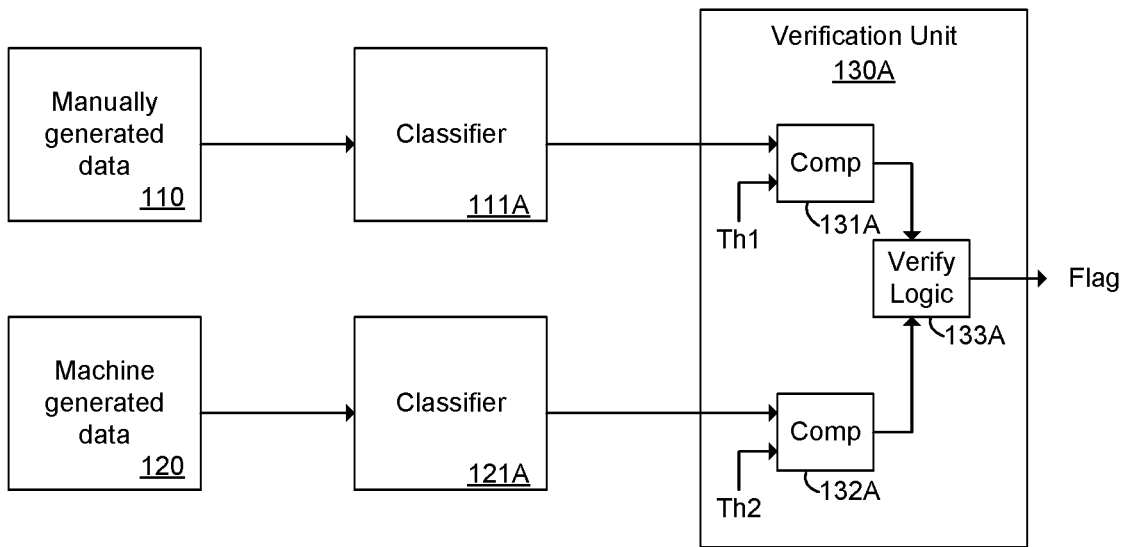
FIG. 1A illustrates a system for verifying medical diagnoses according to one embodiment.

FIG. 1A illustrates a system for verifying medical diagnoses according to one embodiment. Features and advantages of the present disclosure enable a computer system to verify medical diagnoses of a medical professional (e.g., a doctor), generated manually, with machine generated data, for example, which improves medical diagnostics capabilities of computer systems. For instance, a medical diagnosis verification system according to one embodiment may receive manually generated medical data 110 and machine generated medical data 120. Manually generated medical data 110 may include, for example, free-form text, text from one or more fields in an electronic form, or text corresponding to a selection in an electronic form. Such data may be created directly by a doctor (e.g., direct text entry) or using handwriting recognition software (for converting handwritten reports to text) or voice recognition software (for converting voice recorded reports to text), for example. Manually generated medical data 110 may be a doctor's report, radiologist's report, or any other medical professional's report, notes, or similar electronic health records (EHR) about a patient. Machine generated medical data 120 may include, for example, an electronic image, electronic test results, or a video, for example. Machine generated medical data 120 may include X-Rays, ultrasounds (US), magnetic resonance (MM), Nuclear Medicine imaging, positron emission tomography (PET), computed tomography (CT scans), endoscopy (ES), mammograms (MG), digital radiography (DR), phosphor plate radiography, Histopathology, or ophthalmology to name just a few examples.

Typically, a health professional may indicate whether or not a particular patient has, or does not have, a particular diagnosis result. For example, a doctor may determine that a patient has a lung nodule by manually reviewing an image of the patient's lungs. However, if the doctor misses the lung nodule in the image, the patient is put at greater risk. Features and advantages of the present disclosure allow a computer system to analyze manually generated medical data (e.g., a doctor's report) and corresponding machine generated medical data (e.g., the image) to determine if the medical professional missed a diagnosis. For example, manually generated medical data 110 is processed by a first classification unit (or classifier) 111A, and the machine generated medical data 120 is processed by a second classification unit (or second classifier) 121A. In one embodiment, the classifiers 111A and 111B have been trained to detect one particular diagnosis (e.g., the existence or non-existence of a lung nodule). Classifier 111A receives the manually generated medical data 110 and processes the data to generate a first probability that the manually generated medical data 110 indicates a particular medical diagnosis (e.g., the existence or non-existence of a lung nodule). Classifier 121A receives the machine generated medical data 120 and processes the data to generate a second probability that the machine generated medical data 120 indicates the same particular medical diagnosis (e.g., the existence or non-existence of a lung nodule). Manually generated data and machine generated data may be associated (e.g., a doctor's report and an associated image or test data) and related to the same patient, for example. Advantageously, each classifier 111A and 121A may be trained to recognize the same diagnoses so both classifiers output corresponding probabilities for the same patient based on different types of inputs. These probabilities may be input to a verification unit 130A configured to verify the manually generated input data by combining the first and second probabilities, for example. In the embodiment shown in FIG. 1A, the probability from classifier 111A is compared, at 131A, to a first threshold (Th1) to determine if the probability is high enough to result in a positive diagnosis. Similarly, the probability from classifier 111B is compared, at 132A, to a second threshold (Th2) to determine if the probability is high enough to result in a positive diagnosis. Outputs of the threshold comparisons at 131A and 132A are combined logically at 133A to verify the manually generated data 110. For example, if the probability from classifier 111A applied against threshold Th1 indicates a negative diagnosis (e.g., the non-existence of a lung nodule) and the probability from classifier 121A applied against threshold Th2 also indicates a negative diagnosis, then the manually generated data (e.g., the doctor's report) is verified. However, if the probability from classifier 111A applied against threshold Th1 indicates a negative diagnosis (e.g., no lung nodule detected) and the probability from classifier 121A applied against threshold Th2 also indicates a positive diagnosis (e.g., a lung nodule was detected by classifier 121A), then a potential error is detected. For example, in one embodiment, the verification unit 130A generates a verification flag when a probability based on the machine generated data indicates a positive result for a first diagnosis (e.g., there is a lung nodule), and a corresponding probability based on the manually generated data indicates a negative result for the first diagnosis (e.g., no lung nodule). Thus, a flag may be generated indicating that the manually generated data (e.g., the doctor's report) missed the diagnosis, and further remediation may be performed, for example.

Classifiers 111A and 121A may be medical classifiers configured for processing medical input data and generating probabilities corresponding to medical diagnoses. Classifiers 111A and 121A may be machine learning classifiers configured using training sets substantially similar in nature to the types of data inputs they are to receive and process, for example. Classifiers 111A and 121A may be implemented in computer code (instructions executable on a processor) that perform one of a variety of classification algorithms and configured using a training data set, for example.

Figure 1B:
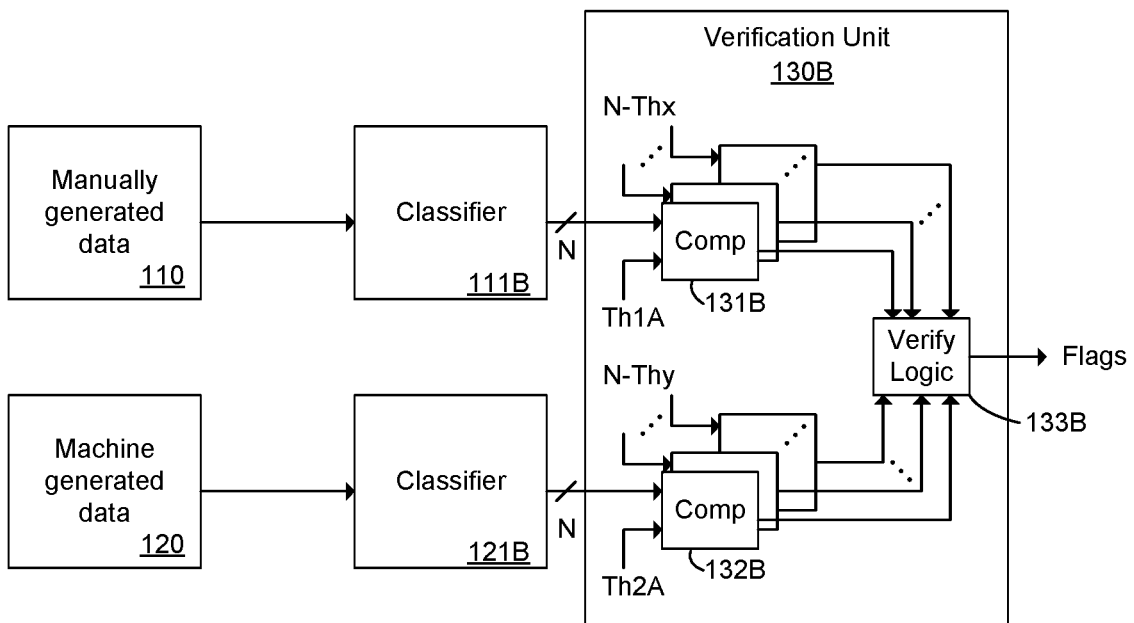
FIG. 1B illustrates a system for verifying medical diagnoses according to one embodiment.

FIG. 1B illustrates another embodiment of a medical diagnostic system according to an embodiment. In this embodiment, classifiers 111B and 121B are both configured to generate a plurality of probabilities corresponding to a plurality of different diagnoses. For example, classifier 111B may receive manually generated medical data 110 and produce probabilities for a lung nodule, a liver nodule, and a kidney nodule. Analogously, classifier 121B may receive machine generated medical data 120 and produce probabilities for a lung nodule, a liver nodule, and a kidney nodule. Each classifier 111B and 121B may produce N probabilities (where N is an integer), where each probability is a likelihood that a particular diagnosis is detected in the manually generated input data or machine generated input data, respectively. Each pair of corresponding probabilities for a particular diagnosis may be compared 131B, 132B against a pair of thresholds ((Th1A, Th2A), (Th1B, Th2B), etc. ... ), as illustrated here in verification unit 130B, for example. One threshold in each pair is applied to the probability from classifier 111B, and the other is applied to the probability from classifier 121B. In one embodiment described in more detail below, corresponding probabilities for a particular diagnosis from classifiers 111B and 121B (e.g., probabilities of a lung nodule based on manual and machine inputs) may be analyzed across a training set of data inputs (manually and machine generated) to generate the thresholds pairs.

The output of each pair of comparisons described above is processed by verification logic 133B, which in some embodiments may generate flags when a negative diagnosis is found in the manually generated data and a positive diagnosis is found for the machine generated data, for example. In one embodiment, different flags generated for different diagnoses may be sent to a user interface to inform a user that the manually generated data may have missed a diagnosis, for example.

Figure 2:
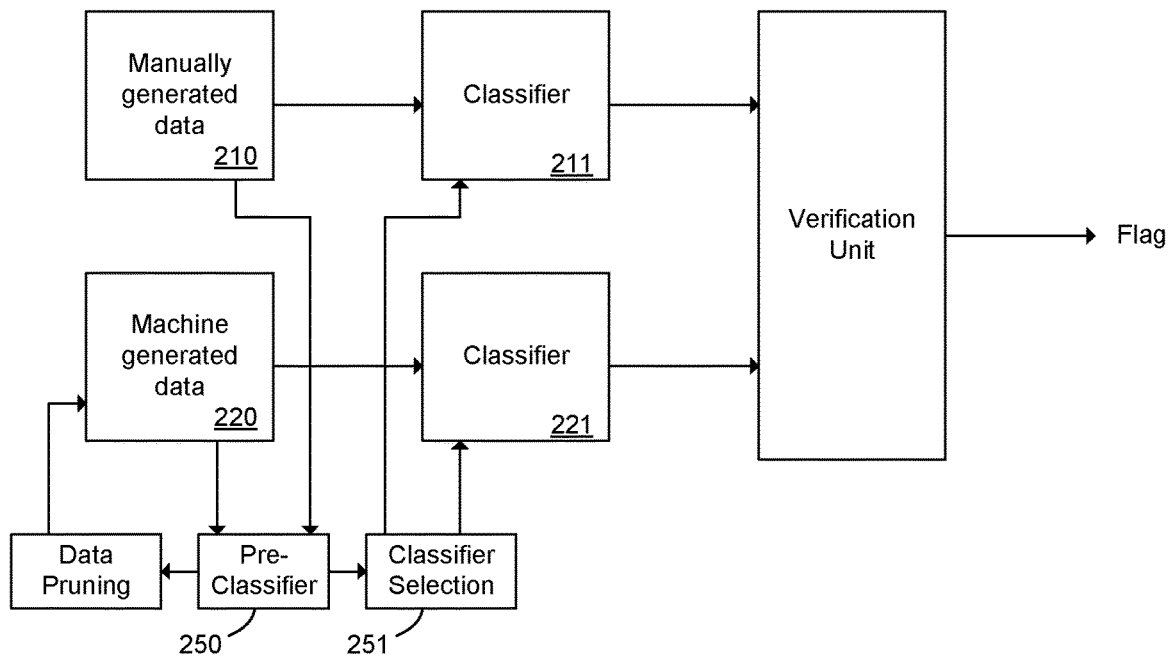
FIG. 2 illustrates a system for verifying medical diagnoses with pre-classification according to one embodiment.

FIG. 2 illustrates a system for verifying medical diagnoses with pre-classification according to one embodiment. Features and advantages of some embodiments of the disclosure include selecting customized classifiers for processing either or both of the manually generated data or machine generated data. For example, a pre-classification process 250 may receive either manually generated medical data 210 or machine generated medical data 220, or both. Further, based on the pre-classifying step, one of a plurality of classifiers may be selected at 251 for classifier 211 for processing the manually generated medical data or for classifier 212 for processing the machine generated medical data.

For example, in one embodiment, if the patient is determined during pre-classification to have a particular condition (e.g., a pre-existing condition), such as cancer, different classifiers may be used to obtain more accurate results in a more computationally efficient manner. For instance, the pre-classification process 250 may be configured to receive manually generated data 210, such as a doctor's report, and determine if the report indicates the patient has or does not have cancer. If a patient is pre-classified as having cancer, a special classifier may be used for classifier 211 that is configured to understand manually generated cancer related terminology (e.g., a cancer specific language classifier), and another special classifier may be used for classifier 221 that has been trained to perform cancer specific diagnoses on cancer patients, for example. Accordingly, the system may determine, from the manually generated medical input data, whether or not a first medical condition is present. Next, first condition specific classifiers may be selected for classifier 211 and classifier 221 when the condition is present (e.g., when the patient has cancer), and second condition specific classifiers may be selected for classifier 211 and classifier 221 when the condition is not present (e.g., patient does not have cancer).

As another example, machine generated data 220 may be processed by a pre-classifier 250 to determine if an image, for example, shows a lung or an abdomen or other body part. Depending on the pre-classification result (e.g., which body part is in the image), a different classifier 221 may be selected. For example, if the body part is a lung, a classifier 221 may be selected that is trained to analyze lungs for lung nodules, and if the body part is an abdomen, a classifier 221 may be selected that is trained to analyze an abdomen for a pancreas nodule, for example.

As yet another example, an electronic health record or image (or both) may be pre-classified to determine if a patient has a metal prosthesis, for example. Accordingly, a different classifier 221 may be used to process machine generated medical data if the patient has a metal prosthesis versus if the patient does not have a metal prosthesis, for example.

As yet another example, a characteristic of a patient may be determined from the manually generated input data and used to select different classifiers for classifier 211 and 221. For example, if the manually generated medical data is analyzed and the patient's gender is determined, different classifiers may be selected for classifiers 211 and 221 based on whether the patient is male or female, for example, to optimize diagnostic analysis. In another embodiment, a patient's age may be used to select different classifiers for classifier 221 to improve diagnostic performance, for example.

As yet another example, the machine generated input data may have associated metadata that indicates a scan type. For example, a scan may be a CT scan, X-Ray, or MM, for example, which may require different classifiers. Accordingly, pre-classification may comprise determining a scan type from the metadata and selecting classifier 221 based on the scan type specified in the metadata. Further, in one embodiment, classifier 211 may also be selected from a plurality of classifiers based on the scan type specified in the metadata. For example, doctors may have particular ways of writing about X-Ray scans that are different than the way they write about CT scans or MM scans. Performance of the system and quality of the results may be enhanced further by selecting particular classifiers 211 trained to process particular manually generated inputs for particular scan types, for example.

The above examples illustrate that, in some embodiments, pre-classification may act as a supervisory layer that analyzes the manually generated data or machine generated data, or both, and coordinates the selection of classifiers 211 and 221 to optimize recognition of diagnoses, for example. Accordingly, pre-classifier 250 may comprise one or more machine learning based classifiers for performing different classification tasks (receiving text or images and determining different aspects of each, such as body part), and pre-classifier 250 may also include logic based classifiers for selecting classifiers 211 and 221 based on various parameters, such as metadata associated with machine generated data or fields in a fillable form, for example. Advantageously, pre-classifying and selecting more precise classifiers for the manually generated data and associated machine generated data produces more precise results and reduces false positives and noise in the system, thereby improving the quality of the combined system, for example.

Figure 3:
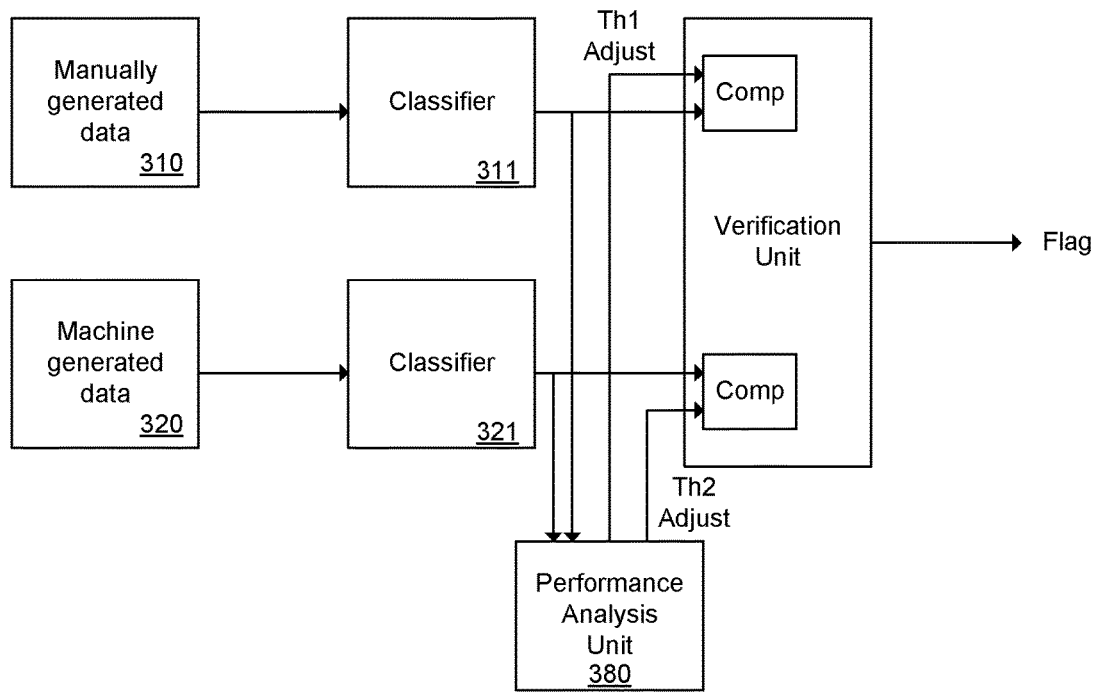
FIG. 3 illustrates a system for verifying medical diagnoses with threshold adjusting according to one embodiment.

FIG. 3 illustrates a system for verifying medical diagnoses with threshold adjusting according to one embodiment. As illustrated above, a wide range of classifiers may be selected and used to process manually generated and machine generated medical data. One aspect of the present disclosure includes determining optimum thresholds to be used to verify a diagnosis. For example, in one embodiment, training data of manually generated medical data inputs 310 and associated machine generated medical inputs 320 are used to determine optimum thresholds for comparison with the probabilities generated by classifiers 311 and 321. For instance, FIG. 3 may include a performance analysis unit 380. Performance analysis may include determining, based on a training data set, one or more first thresholds configured to determine if one or more probabilities from classifier 311 result in a positive result for a corresponding one or more diagnoses. Additionally, performance analysis may include determining, based on the training data set, one or more second thresholds configured to determine if one or more probabilities from classifier 321 result in a positive result for the corresponding one or more diagnoses. For the simple case of classifiers 311 and 321 each generating one probability corresponding to one diagnosis (e.g., lung nodules), performance analysis unit 380 may comprise processing training data for numerous reports and associated images in classifiers 311 and 312 to obtain probabilities relating to the diagnosis (e.g., relating to lung nodules). The training data results may be used to set Th1 and Th2 to obtain improved overall system performance. In one embodiment, false positive rates (a correct diagnosis based on manual data, but an incorrect diagnosis based on machine data), true positive rates (incorrect diagnosis based on manual data, but correct diagnosis based on machine data), and receiver operating characteristic (ROC) curves may be applied to determine optimum thresholds Th1 and Th2 to improve the accuracy of the combined classifiers 311 and 321, for example.

It is to be understood that the classification units, verification units, pre-classifiers, performance analysis units, comparison units, and other components described herein may be implemented as software components implemented as program code and instructions executable on one or more computer processors, for example.

Figure 4:
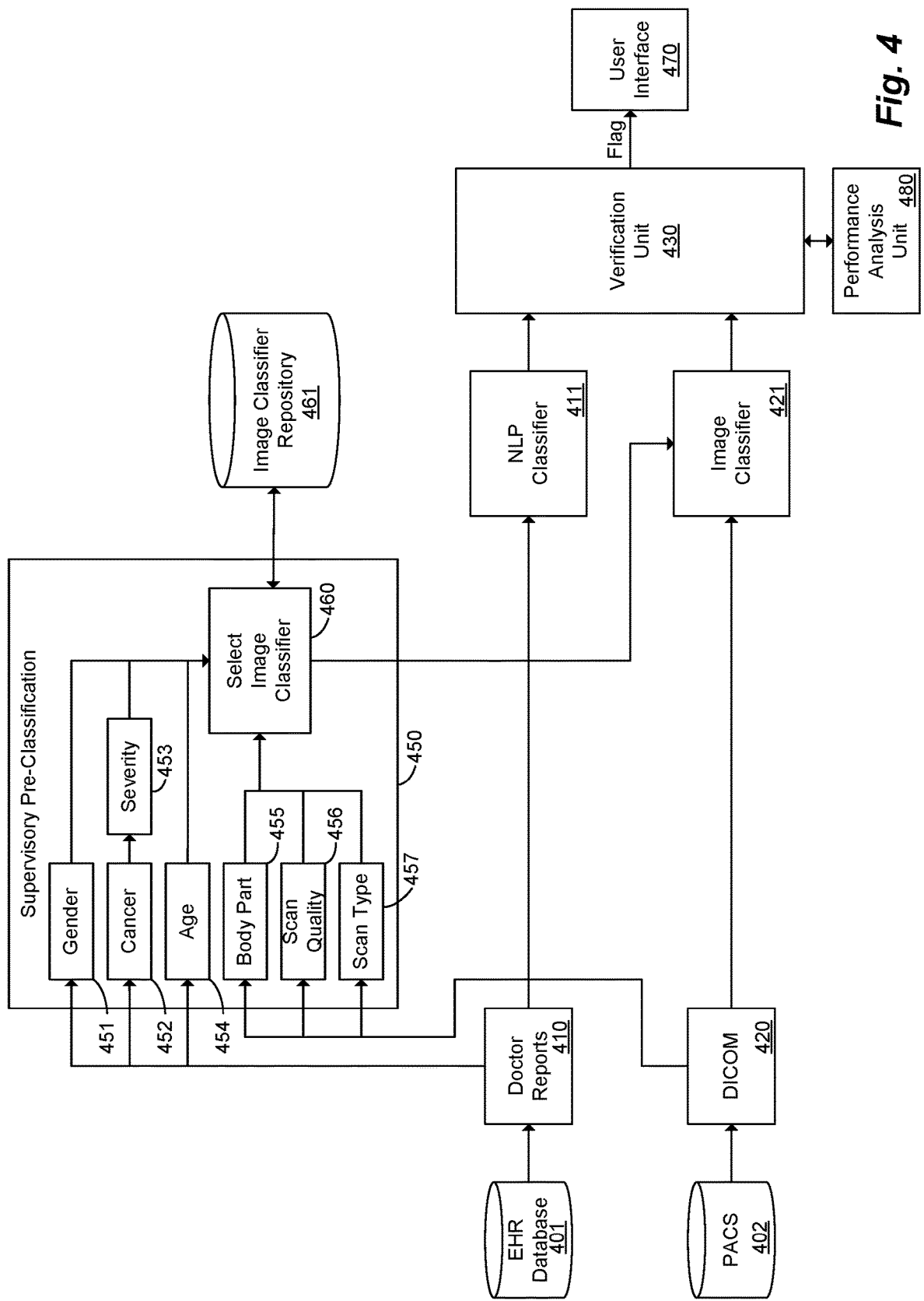
FIG. 4 illustrates an example system for verifying medical diagnoses according to another embodiment.

FIG. 4 illustrates an example system for verifying medical diagnoses according to another embodiment. In this example, manually generated medical data comprises electronic health records (EHR) stored in one or more EHR databases 401, and machine generated medical data comprises picture archiving and communication system (PACS) 402 for storing and accessing medical electronic images, for example. DICOM (Digital Imaging and Communications in Medicine) is a standard for storing and transmitting medical images. In this example, doctor's reports 410 for a patient and associated DICOMs (images) 420 for the patient are extracted from EHR database 401 and PACS 402, respectively. Reports 410 and DICOMs 420 may be sent to supervisory pre-classifier 450 for processing to determine an appropriate classifier to achieve optimum overall system results, for example. For example, doctor's reports 410 may be analyzed for gender 451, pre-existing cancer 452 and severity 453, and/or age 454, for example. Accordingly, gender, age, and the existence/non-existence of cancer, and its severity, may be used to select an image classifier at 460, for example. Similarly, electronic images (DICOMs) 420 may be pre-classified for a body part 455, scan quality 456, and/or scan type 457, for example, and the results used to select an image classifier 460. In this example, different classifier models may be stored in an image classifier repository 461, and an optimum classifier 421 may be selected and used for classification of the DICOMs 420. Similarly, pre-classification processes may be used for selecting an natural language processing (NLP) classifier 411 in other embodiments, and the example shown here is merely illustrative.

Doctor's reports, in some embodiments, may be free form text. In this example, such reports 410 are processed by a natural language processor (NLP) classifier 411 trained to classify manually generated reports into one or more particular diagnoses (e.g., lung nodule—yes/no). Accordingly, NLP classifier 411 outputs one or more probabilities, where each probability corresponds to one diagnosis that classifier 411 is trained to analyze. Each probability is a number representing the probability that a particular diagnosis exists based on the input report 410, for example. Similarly, a DICOM 420 for the same patient, which is associated with the doctor's report processed by NLP classifier 411, may be processed by an image classifier 421. Image classifier 421 likewise outputs one or more probabilities, where each probability corresponds to one diagnosis classifier 421 is trained to recognize. Advantageously, each classifier 411 and 421 is trained to recognize the same diagnoses so both classifiers output corresponding probabilities for the same diagnosis and same patient based on different types of inputs. Each probability is a number representing the probability that a particular diagnosis exists based on the input report 410 and image 420, for example.

Verification unit 430 receives the probabilities from NLP classifier 411 and image classifier 421. Verification unit 430 may receive threshold pairs for each set of like probabilities from performance analysis unit 480, for example. When a probability output by each classifier 411 and 421 for the same diagnosis meets a particular threshold, the diagnosis is deemed to have been detected by the classifier based on the input data. Performance analysis unit 480 may generated one set of threshold pairs (th1A, th2A) having different values for probabilities generated by classifiers 411 and 421 for one diagnosis (e.g., lung nodules), and performance analysis unit 480 may generated another set of threshold pairs (th1B, th2B) having different values for probabilities generated by classifiers 411 and 421 for another diagnosis (e.g., liver nodules), for example. Each pair of thresholds may be generated based on analyzing training sets of manually generated data (e.g., doctor's reports) and corresponding machine generated data (e.g., DICOM images) for each particular diagnosis to generate optimum threshold pair values for each diagnosis to maximize the accuracy of one or more flags generated when image classifier 421 detects a particular diagnosis and NLP classifier 411 does not detect the same diagnosis. The one or more flags may be used to present information in a user interface 470 to inform a user that a doctor's report may have missed a diagnosis, for example.

Figure 5:
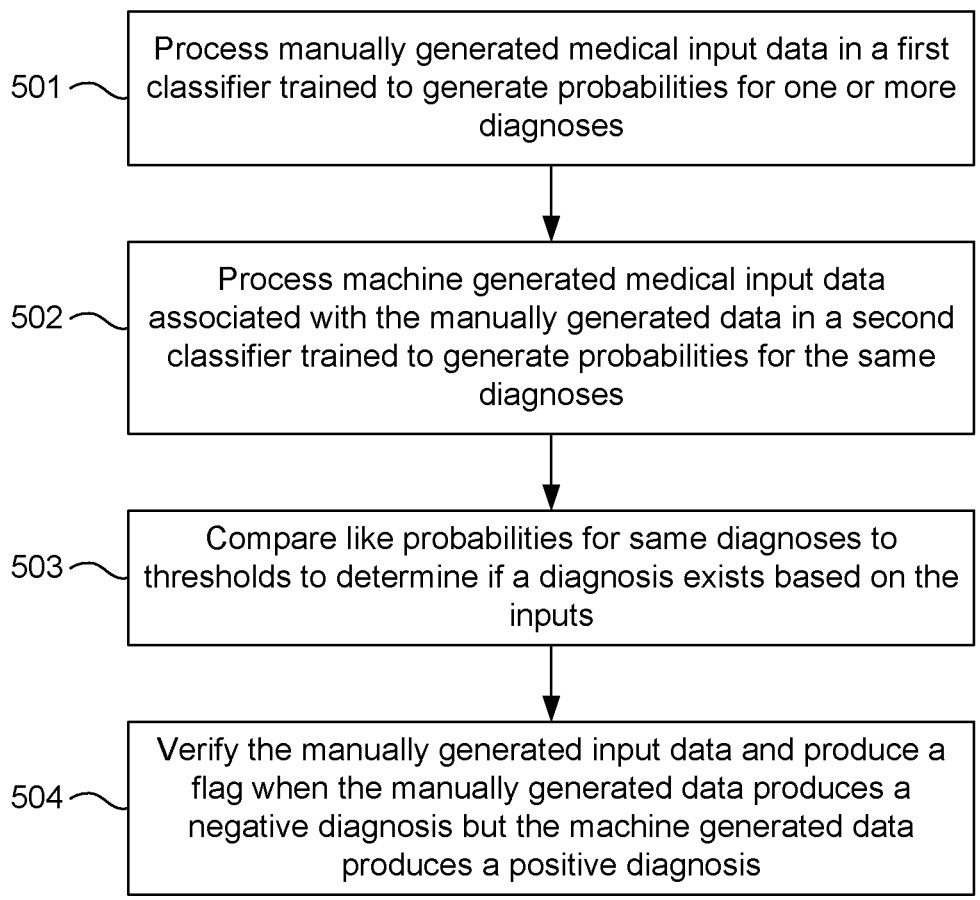
FIG. 5 illustrates a method of verifying a diagnosis according to one embodiment.

FIG. 5 illustrates a method of verifying a diagnosis according to one embodiment. At 501, manually generated medical input data is processed in a first classifier trained to generate probabilities for one or more diagnoses. At 502, machine generated medical input data associated with the manually generated data is processed in a second classifier trained to generate probabilities for the same diagnoses. At 503 like probabilities (e.g., probabilities for the same diagnosis) are compared to separate thresholds (e.g., threshold pairs for each diagnosis) to determine if a particular diagnosis is detected by each classifier based on of the manual/machine inputs. At 504, the manually generated input data is verified and a flag (e.g., a notification, message, or other software indicator) is generated when the manually generated input data produces a negative diagnosis but the machine generated input data produces a positive diagnosis.

Figure 6:
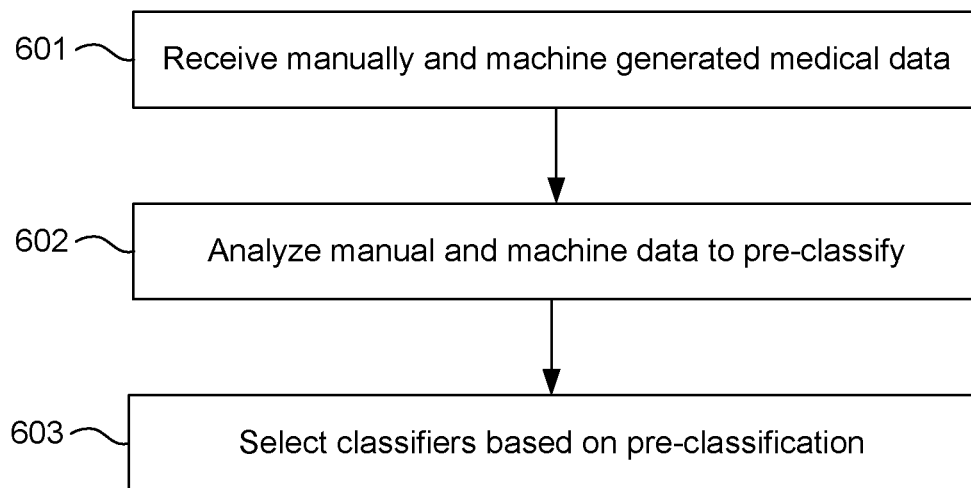
FIG. 6 illustrates a method of verifying a diagnosis according to another embodiment.

FIG. 6 illustrates a method of verifying a diagnosis according to another embodiment. At 601, manually generated medical data and associated machine generated medical data are received in supervisory pre-classification unit. At 602, the manual and machine generated data is analyzed to pre-classify each related pair of manual/machine data sets. At 603, classifiers may be selected based on the pre-classification to improve the accuracy of the system.

Figure 7:
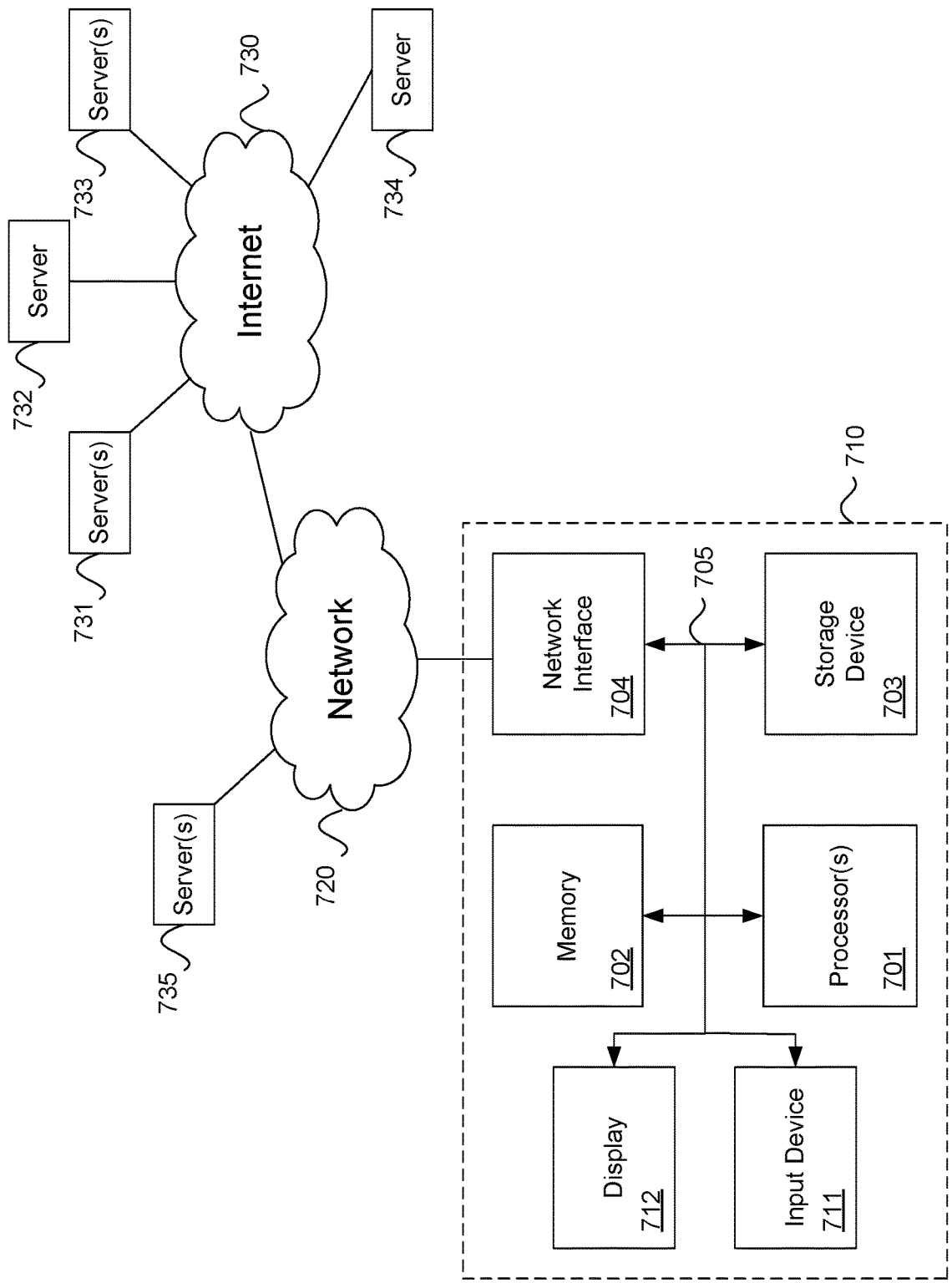
FIG. 7 illustrates computer hardware for executing software according to various embodiments.

FIG. 7 illustrates computer hardware for executing software according to various embodiments. The following hardware description is merely one illustrative example. It is to be understood that a variety of computers topologies may be used to implement the techniques disclosed herein. An example computer system 710 is illustrated in FIG. 7. Computer system 710 includes a bus 705 or other communication mechanism for communicating information, and one or more processor(s) 701 coupled with bus 705 for processing information. Computer system 710 also includes a memory 702 coupled to bus 705 for storing information and instructions to be executed by processor 701. Memory 702 may also be used for storing programs executed by processor(s) 701. Possible implementations of memory 702 may be, but are not limited to, random access memory (RAM), read only memory (ROM), or both. A storage device 703 is also provided for storing information and instructions. Common forms of storage devices include, for example, a hard drive, a magnetic disk, an optical disk, a CD-ROM, a DVD, a flash or other non-volatile memory, a USB memory card, or any other medium from which a computer can read. Storage device 703 may include source code, binary code, or software files for performing the techniques above, for example. Storage device 703 and memory 702 are both examples of non-transitory computer readable storage mediums.

Computer system 710 may be coupled via bus 705 to a display 712 for displaying information to a computer user. An input device 711 such as a keyboard, touchscreen, mouse and/or camera is coupled to bus 705 for communicating information and command selections from the user to processor 701 (e.g., in a software generated user interface). The combination of these components allows the user to communicate information with the system. In some systems, bus 705 represents multiple specialized buses for coupling various components of the computer together, for example.

Computer system 710 also includes a network interface 704 coupled with bus 705. Network interface 704 may provide two-way data communication between computer system 710 and a local network 720. Network 720 may represent one or multiple networking technologies, such as Ethernet, local wireless networks (e.g., WiFi), or cellular networks, for example. The network interface 704 may be a wireless or wired connection, for example. Computer system 710 can send and receive information through the network interface 704 across a wired or wireless local area network, an Intranet, or a cellular network to the Internet 730, for example. In some embodiments, a browser or local application, for example, may access data and features on backend software systems that may reside on multiple different hardware servers on-prem 735 or across the Internet 730 on servers 731-734. One or more of servers 731-734 may also reside in a cloud computing environment, for example. Such servers may also comprise hardware such as memory, one or more processors, storage devices, buses, and a network interface, for example. In various embodiments, the above techniques may be implemented in an on-prem or cloud based server system, where machine generated and manually generate data is stored and the above techniques are performed on servers. The one or more flags mentioned above may be sent from a backend system on one or more servers to a local client on computer 710, for example, to notify a user of a discrepancy between a manually generated medical record and a related machine generated medical image, for example.

The discussion will turn to a description of configuring a multi-classifier classification system in accordance with the present disclosure. The foregoing verification systems are examples of multi-classifier classification systems. The system shown in FIG. 1A, for example, represents a dual-classifier classification system that comprises a first component classifier 111A for classifying manually generated medical data (e.g., a doctor's written report) and a second component classifier 111B for classifying machine generated medical data (e.g., X-rays, ultrasound, etc.). Although medical data will be used as examples, it will be appreciated that multi-classifier classification systems in accordance with the present disclosure can be applied to any suitable classification problem.

Figure 8:
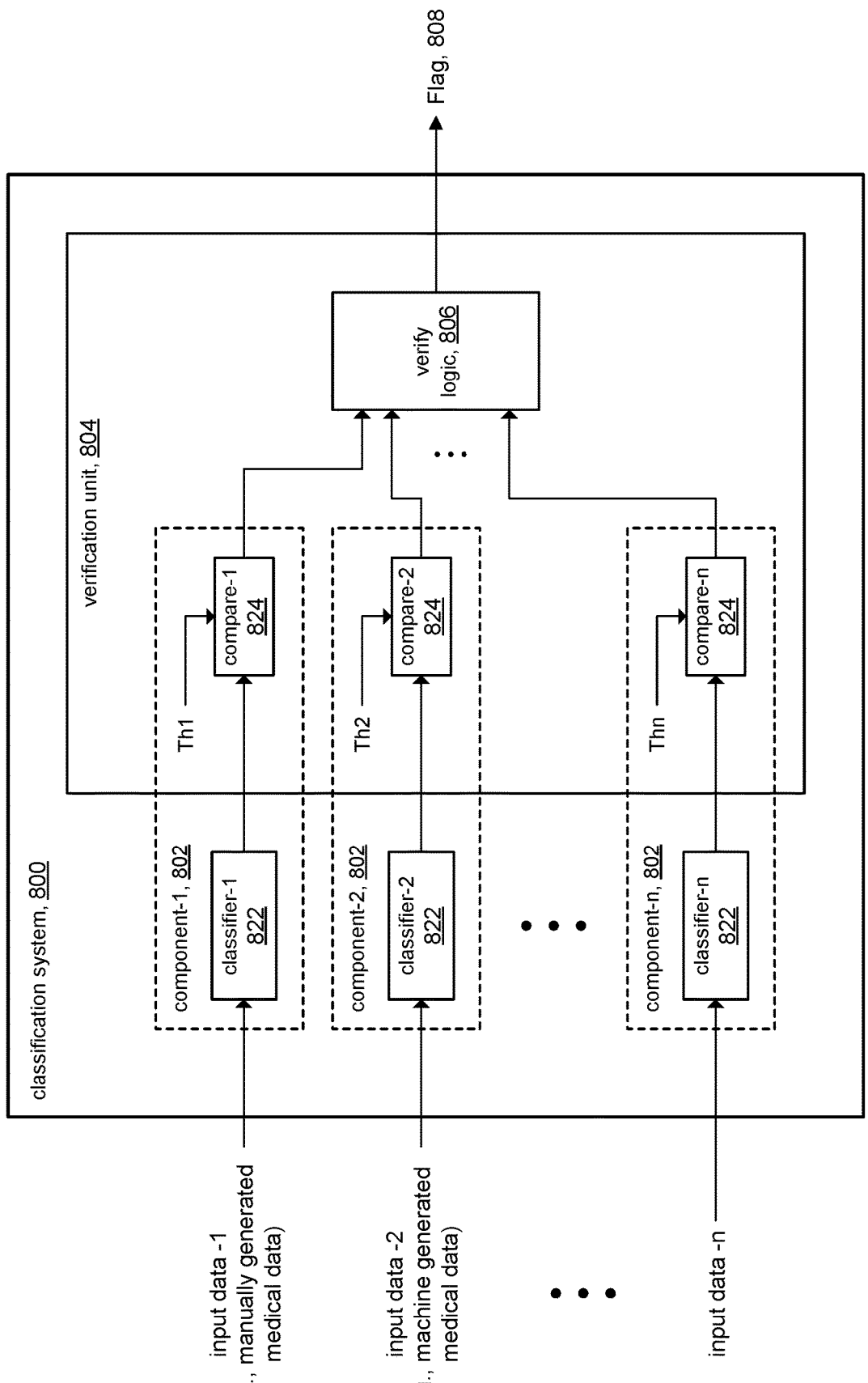
FIG. 8 illustrates a multi-classifier classification system according to some embodiments of the present disclosure.

FIG. 8 shows a multi-classifier classification system 800 in accordance with some embodiments of the present disclosure. The multi-classifier classification system 800 represents a generalization of the foregoing two-classifier classification systems (e.g., FIGS. 1A and 4) to more than two component classifiers. In accordance with the present disclosure, the multi-classifier classification system 800 can comprise any number n of component classifiers 802. In some embodiments, for example, each component classifier 802 is a binomial (binary) classifier that outputs a binary classification decision; e.g., positive class, negative class.

Each component classifier 802 can comprise a classifier element 822 and a corresponding comparator unit 824. FIG. 8 shows for example that classifier element classifier-1 has a corresponding comparator unit compare-1. Likewise, classifier-12 has a corresponding comparator unit compare-2, and so on. Each comparator unit 824 can compare the output of its corresponding classifier element 822 with a corresponding reference referred to as a decision threshold (decision boundary), Th1, Th2, . . . Thn, to produce a binary classification decision. Consider, for example, component classifier component-1 comprising classifier element classifier-1 and corresponding comparator unit comp-1. Classifier-1 will process its input data to produce an output value; for example, the input data may be processed by classifier-1 according to a logistic regression algorithm to produce a real valued output (probability) in the range 0.00 to 1.00. Comp-1 will output a binary decision (e.g., positive or negative) based on whether that real valued output from classifier-1 is greater than or less than its corresponding decision threshold Th1. The decision threshold Th1 can be said to configure the classifying operation of the component classifier component-1; changing the value of Th1 affects the output (i.e., operation) of component classifier component-1. Generally, the decision thresholds Th1, Th2, Thn configure each of the corresponding component classifiers 802.

The multi-classifier classification system 800 can include a verification unit 804 that provides the same functionality and processing as described above, for example, in connection with verification unit 130A in FIG. 1A. Verification unit 804, however, is configured to accommodate n component classifiers 802, while verification unit 130A shown in FIG. 1A is configured to accommodate two component classifiers 111A, 121A.

In some embodiments, the n comparator units 824 that comprise the component classifiers 802 can be incorporated in the verification unit 804. The verification unit 804 can further include verify logic 806, which functions in the same manner as verify logic 133A shown in FIG. 1A. In some embodiments, verify logic 806 can be configured to verify input data provided to one or more of the component classifiers 802. The verify logic 808 can output a flag 808 to indicate an outcome of the verification.

Figure 9:
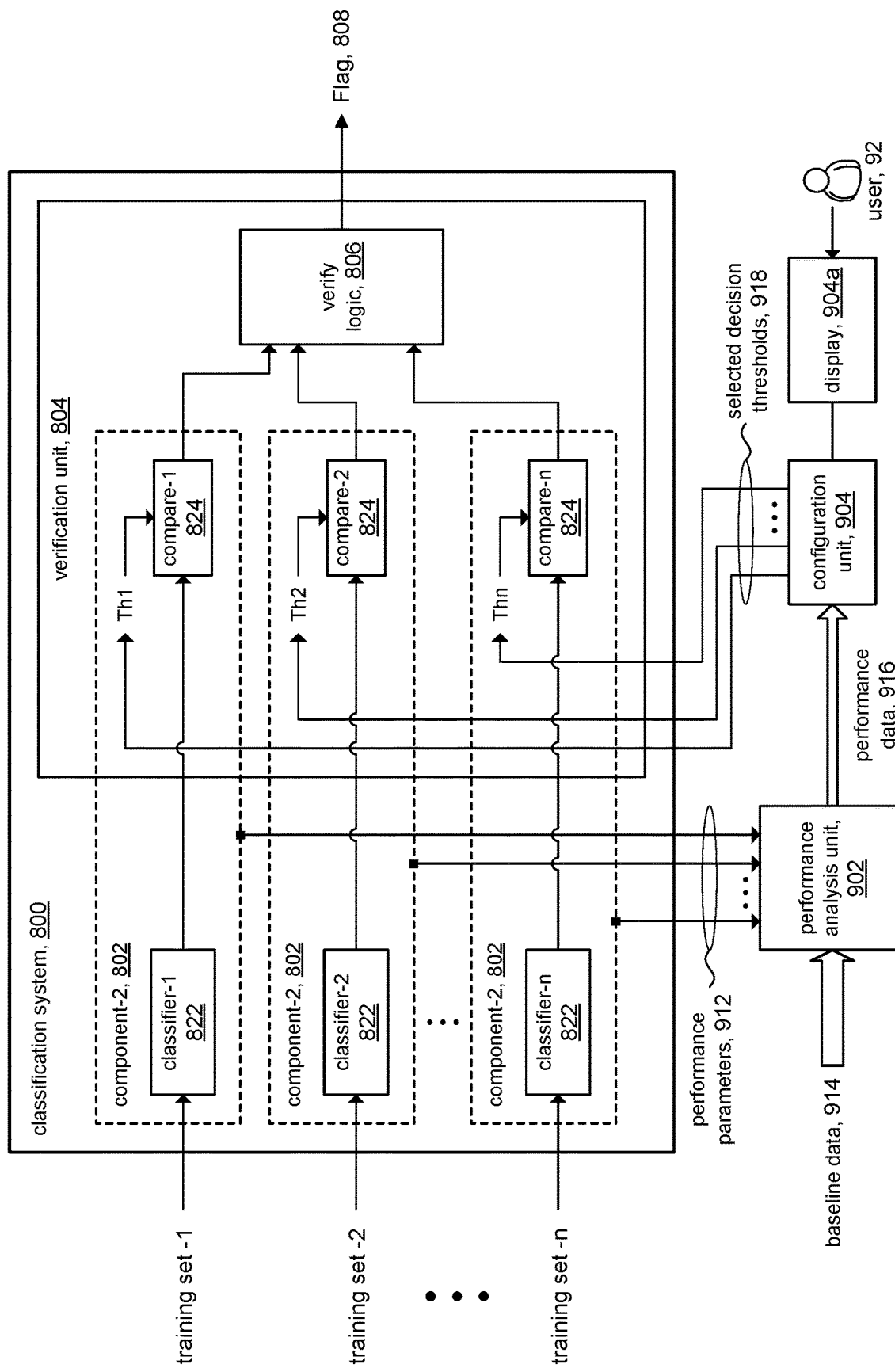
FIG. 9 illustrates an embodiment for configuring a multi-classifier classification system according to some embodiments of the present disclosure.

FIG. 9 shows an illustrative embodiment for configuring a multi-class classification system in accordance with the present disclosure. In some embodiments, for example, multi-classifier classification system 800 can include a performance analysis unit 902 and a configuration unit 904. The performance analysis unit 902 can generate system-level performance data 916 that characterizes operation of the multi-classifier classification system 800. As will be discussed in more detail below, the performance data 916 can be based on performance parameters 912 that characterize operation the component classifiers 802 and baseline data 914.

Performance parameters 912 that characterize the operation of a component classifier 802 can be any metric that evaluates how well a classifier element 812 performs when presented with a training set. For example, the performance of classifiers used in the medical field (e.g., medical diagnosis) are often assessed using sensitivity and specificity metrics. Classifiers in computer application (e.g., search engines) can be assessed in terms of precision and recall metrics.

In some embodiments, performance parameters 912 can include a true positive rate (TPR) metric and a false positive rate (FPR) metric to assess performance of each component classifier 802. The TPR metric is also referred to as "sensitivity," which measures the proportion of actual (true) positives that are correctly identified as such. In the context of the lung nodule example used in the present disclosure, for instance, a true positive event occurs when a doctor correctly diagnoses the presence of lung nodules in a patient. On the other hand, the FPR measures the proportion incorrectly identified positives. Using the lung nodule example, for instance, a false positive event occurs when the doctor reports the presence of lung nodules when the patient in fact does not have lung nodules.

The TPR for a component classifier 802 can be referred to as a "component" TPR to distinguish from a "system" TPR (discussed below). The component TPR for a component classifier 802 (e.g., classifier-1) can be a TPR that characterizes the component classifier when it is configured with a given decision threshold and presented with a training data set (e.g., training set-1). In other words, when the component classifier is configured with a particular decision threshold (e.g., $Th_{value}$) and then presented with a training data set, then:

TPR can be the ratio of $D_{pos}$ to $A_{pos}$, and

FPR can be the ratio of $D_{neg}$ to $A_{neg}$, where $D_{pos}$ is the number correctly decided positives made by the classifier, $D_{neg}$ is the number incorrectly decided positives made by the classifier, $A_{pos}$ is the number of actual positives in the training set, and $A_{neg}$ is the number of actual negatives in the training set. These aspects of the present disclosure are discussed in more detail below.

Baseline data 914 can include data separate from the component classifiers 802. Baseline data 914 can be obtained or otherwise derived from data sources external to the multi-classifier classification system 800, such as professional journals, scientific literature, national or worldwide statistics, and so on.

The performance analysis unit 902 can generate system-level performance data 916 based at least on the performance parameters 912 and baseline data 914. The system-level performance data 916 represent a measure of performance of the multi-classifier classification system 800 as a whole. Each data record can be associated with a performance level that is based on a system TPR and a system FPR. A system TPR can be a TPR that characterizes the multi-classifier classification system 800 when its component classifiers 802 are configured with a given set of decision thresholds, and likewise, a system FPR can be an FPR that characterizes the multi-classifier classification system 800 when its component classifiers 802 are configured with the same given set of decision thresholds. These aspects of the present disclosure are discussed in more detail below.

The performance analysis unit 902 can provide the system-level performance data 916 to the configuration unit 904. In some embodiments, the system-level performance data 916 can be receiver operating characteristics (ROC) data comprising pairs of system TPRs and system FPRs along with corresponding decision threshold for the component classifiers 802. The configuration unit 904 can present the system-level performance data 916 in a suitable manner that allows a user 92 to view the system-level performance data 916 and select a set of decision threshold values 918 with which to configure the component classifiers 802 that comprise the multi-classifier classification system 800. In some embodiments, for example, the configuration unit 904 can include a display device 904a to present the system-level performance data 916. The configuration unit 904 can configure each component classifier 802 with its respective decision threshold, for example, by storing the decision threshold in a memory of the corresponding comparator unit 824.

Figure 10:
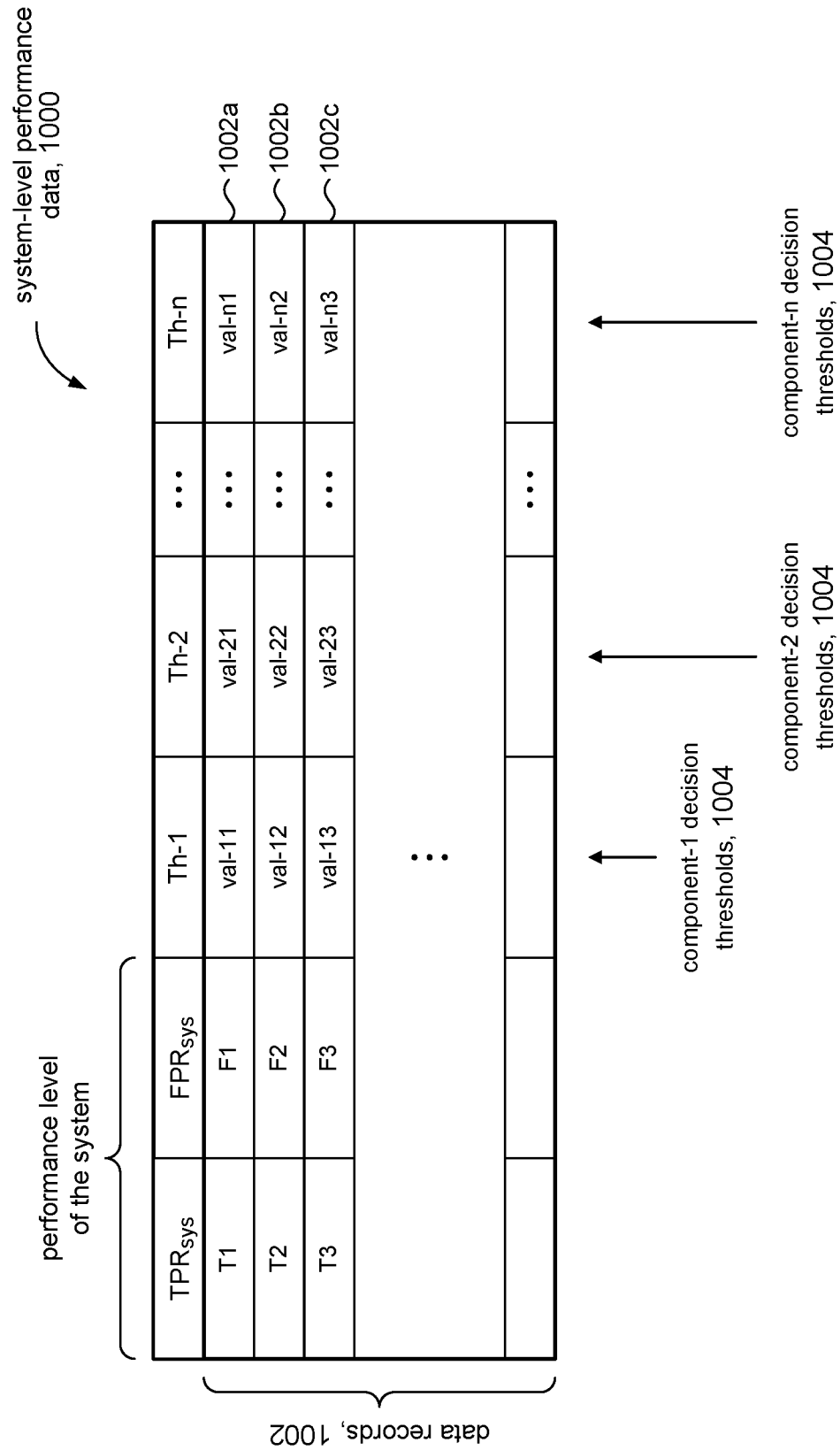
FIG. 10 illustrates an example of system-level performance data according to some embodiments of the present disclosure.

FIG. 10 shows an example of performance data 1000 that can be generated by the performance analysis unit 902 in accordance with the present disclosure. In some embodiments, for example, the performance data 1000 can comprise data records 1002. Each data record is associated with a performance level of the multi-classifier classification system 800, and in some embodiments can include a set of decision thresholds (Th1, Th2, Thn) for the component classifiers 802 that comprise the multi-classifier classification system 800. The performance level can be represented by a system TPR and a system FPR for a given set of decision thresholds. For example, the system TPR in a given data record represents a TPR that characterizes the multi-classifier classification system 800 when its component classifiers 802 are configured with the decision thresholds in the given data record. Likewise, system FPR represents an FPR that characterizes the multi-classifier classification system 800 when its component classifiers 802 are configured with the decision thresholds in the given data record. The performance data 1000 can be provided to the configuration unit 904 in any suitable format. In some embodiments, for example, the performance data 1000 can be stored in a .csv file as lies of comma separate values.

Figure 11:
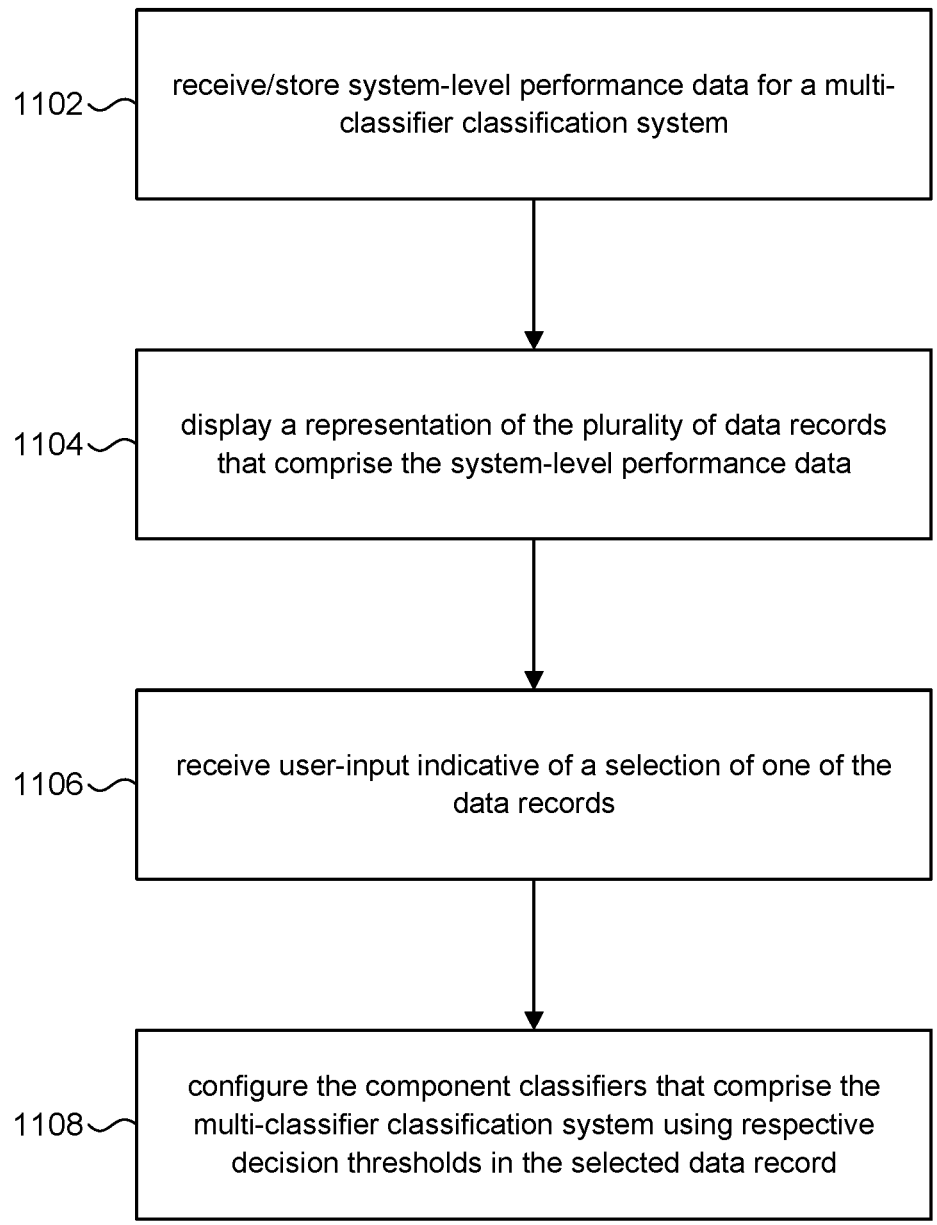
FIG. 11 illustrates an example of operations for configuring a multi-classifier classification system according to some embodiments of the present disclosure.

Referring to FIG. 11, the discussion will now turn to a high level description of processing in the configuration unit 904 (FIG. 9) for configuring the multi-classifier classification system 800 in accordance with the present disclosure. In some embodiments, for example, the configuration unit 904 can include computer executable program code, which when executed by a processor (e.g., 701, FIG. 7), can cause the processor to perform the operations in accordance with FIG. 11. The flow of operations performed by the processor is not necessarily limited to the order of operations shown.

At operation 1102, configuration unit 904 can receive system-level performance data (e.g., 1000, FIG. 10) that is representative of the performance of multi-classifier classification system 800. In some embodiments, for example, the system-level performance data can be data records that comprise ROC data. The configuration unit 904 can store the received data for further processing.

At operation 1104, configuration unit 904 can present a representation of the data records that comprise the received performance data in a suitable user interface (UI) to a user, allowing the user to scan through the data records. In some embodiments, for example, the UI can allow the user to scan the data records in terms of the system TPR or in terms of the system FPR to decide on a combination of system TPR and system FPR. Examples of UI's are discussed below.

At operation 1106, configuration unit 904 can receive input from the user via the UI. Input received from the user identifies a data record selected from among the data records comprising the received system-level performance data. The selected data record indicates the user's selected level of performance of the multi-classifier classification system 800 vis-à-vis the system TPR and FPR parameters contained in the selected data record.

At operation 1108, configuration unit 904 can configure the component classifiers 802 that comprise the multi-classifier classification system using decision threshold values contained the selected data record. As can be seen in FIG. 10, each data record includes a set of decision thresholds 1004. The configuration unit 904 can configure each of the component classifiers 802 that comprise the multi-classifier classification system 800 with corresponding decision thresholds contained in the selected data record.

The configured multi-classifier classification system 800 can now be operated according to the configured component classifiers 802. Recall from the discussion of FIG. 9 that the system TPR and FPR parameters contained in the selected data record represent a performance level of the multi-classifier classification system 800 when it is presented with the training set. Accordingly, to the extent that the training set is representative of actual data that may be presented to the multi-classifier classification system 800, these system TPR and FPR parameters contained in the selected data record can be deemed to represent an expected performance level of the multi-classifier classification system 800 when presented with actual data. Stated differently, the performance level of the multi-classifier classification system 800 with actual data may be approximated by the system TPR and FPR parameters contained in the selected data record.

Figure 12:
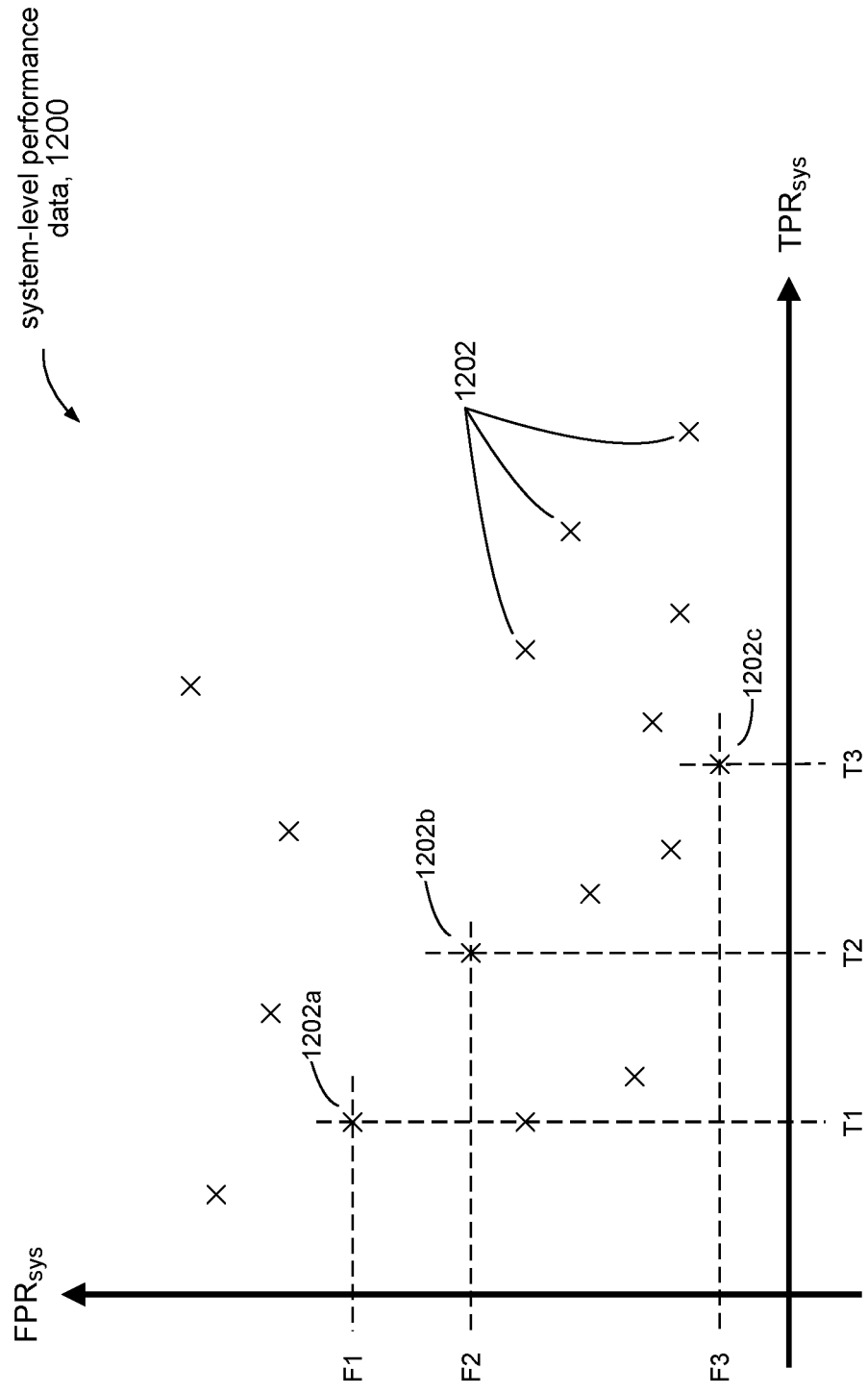
FIG. 12 illustrates a graphical representation of performance data.

FIG. 12 illustrates an example of a graphical representation of system-level performance data of multi-classifier classification system 800. In some embodiments, performance can be expressed by the parameters TPR and FPR that characterize the multi-classifier classification system 800 for a given set of decision thresholds used to configure the component classifiers 802. Performance data can be represented as a table of data records, such as shown in FIG. 10 for example.

FIG. 12 can be a graph 1200 that represents the data records 1002 in FIG. 10. Each point 1202 plotted on the graph 1200 can represent a data record 1002, where one axis of the graphs represents system TPR and another axis represents system FPR. Each point 1202 can be associated with a data record 1002 and plotted on the graph 1200 according to the system TPR and system FPR contained in the data record. Each data point 1202 can be associated with the set of decision thresholds contained in the corresponding data record. Data point 1202a, for example, corresponds to decision thresholds val-11, val-21, . . . val-n1 contained in data record 1002a. Data point 1202b corresponds to decision thresholds val-12, val-22, . . . val-n2 contained in data record 1002b, data point 1202c corresponds to data record 1002c, and so on.

Figure 13:
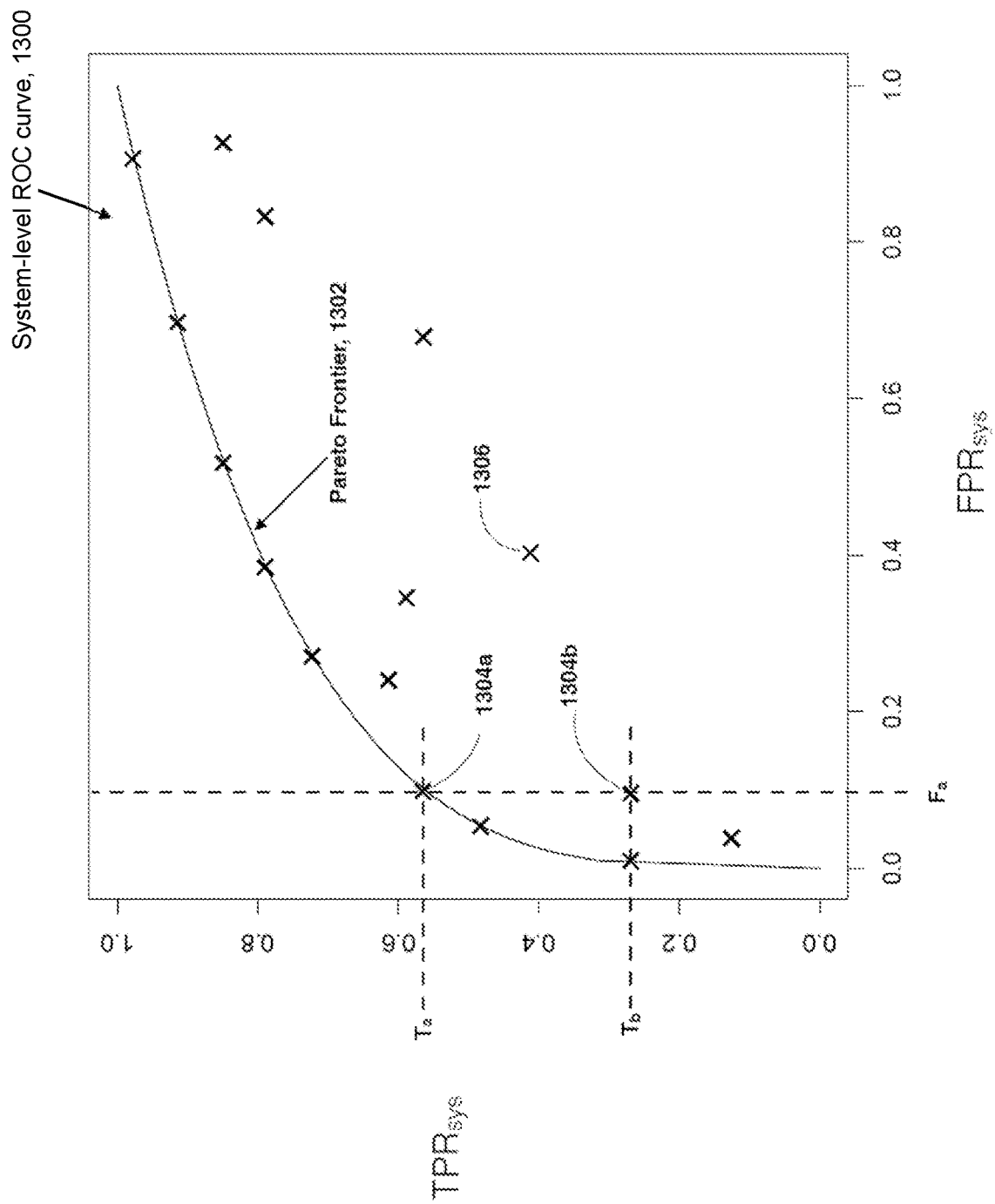
FIG. 13 illustrates an example of a Pareto Frontier.

FIG. 13 illustrates an example of an ROC curve that can be derived from the performance data (e.g., 1000, FIG. 10) for multi-classifier classification system 800. In some embodiments, for example, the ROC curve can be defined as a Pareto Frontier of the data points corresponding to the data records comprising the performance data. The Pareto Frontier, or Pareto set, is a well understood notion that refers to the set of choices that optimizes a system. In the context of the present disclosure, recall that the TPR measures the proportion of actual positives that are correctly identified as such, which is a desirable characteristic of the multi-classifier classification system 800. In contrast, the FPR measures the proportion incorrectly identified positives, which is an undesirable characteristic of the multi-classifier classification system 800. As such, the multi-classifier classification system 800 can be deemed to be optimized when the component classifiers 802 are configured such that the system TPR is maximal and the system FPR is minimal.

However, improving system TPR can increase system FPR and vice versa, and so there may be no configuration of component classifiers 802 that optimizes both the system TPR and the system FPR of the multi-classifier classification system 800. A Pareto Frontier for the multi-classifier classification system 800 comprises a subset (Pareto set) of the data records from the performance data, where for each data record in the subset there is no other data record in the performance data that has both a higher system TPR and a lower system FPR. FIG. 13 shows a system-level ROIC curve 1300 comprising Pareto Frontier 1302 for the example of data points shown in FIG. 12. Consider, for example, data points 1304a and 1304b where both data points have the same FPR ($F_a$) but different TPRs ($T_a$, $T_b$). Data point 1304a is on the Pareto Frontier because there are no other data points that have a lower FPR and a higher TPR. Data point 1304b is not on the Pareto Frontier 1302 because there is a data point, namely, data point 1304a, that has a lower TPR than data point 1304b. As another example, data point 1306 is not on the Pareto Frontier because there are other data points that have either a higher TPR or a lower FPR.

Figure 14:
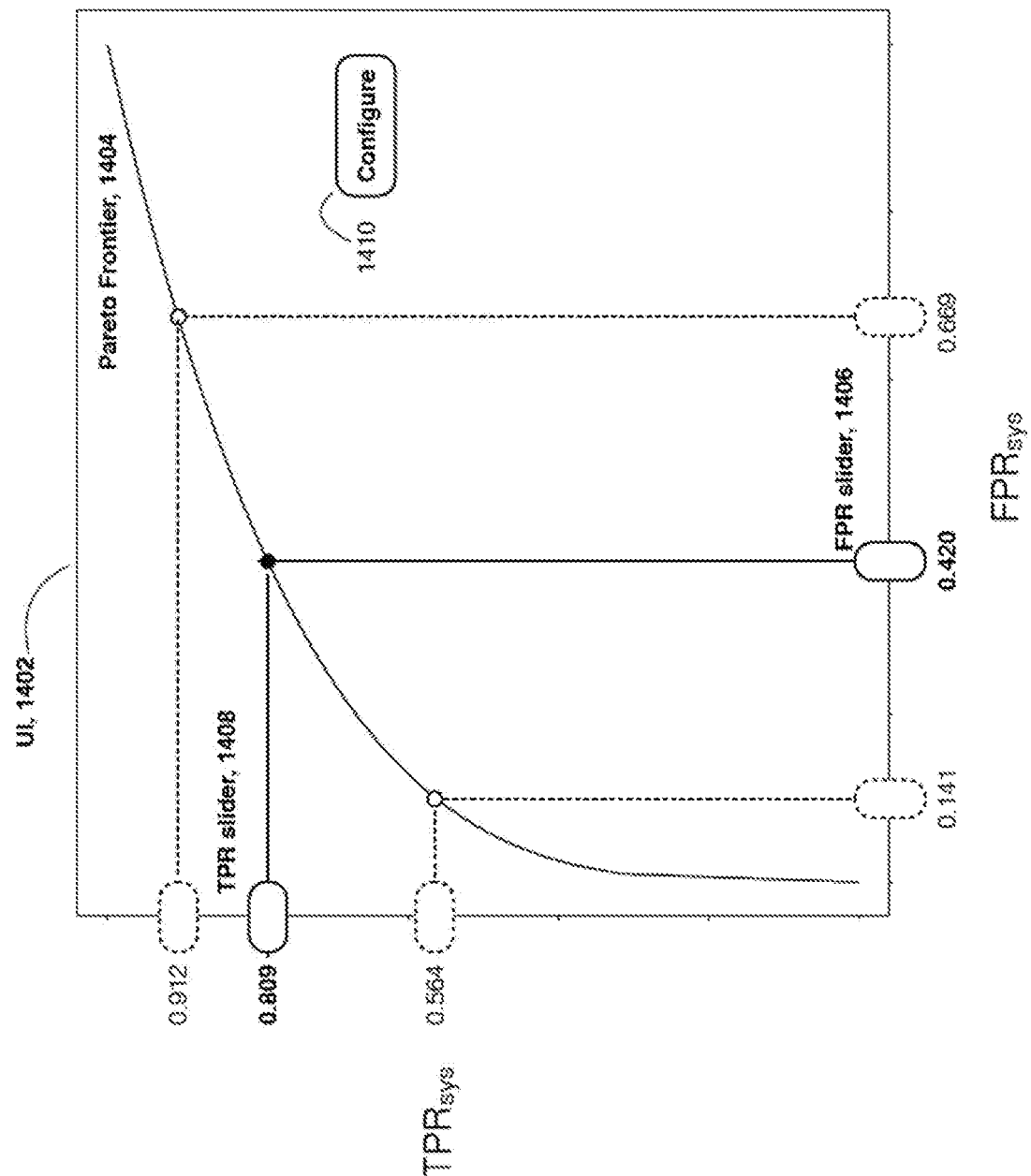
FIGS. 14 and 15 illustrate examples of user interfaces.

FIG. 14 illustrates an example of a user interface (UI) 1402 that the configuration unit 904 can display on display device 904a to present a representation of the performance data for multi-classifier classification system 800 in accordance with the present disclosure. In some embodiments, for example, the UI 1402 can display a graph (Pareto Frontier) 1404 that plots the system TPR against the system FPR contained in the Pareto subset of data records that comprise the performance data. The graph 1404 is discrete; each data point is plotted from the system TPR and system FPR contained in the corresponding data record. For example, the data point at FPR=0.141, TPR=0.564 corresponds to a data record containing a system FPR of 0.141 and a system TPR of 0.564; and likewise for the other data points plotted on graph 1404.

Sliders 1406, 1408 can be used to select a data point on the graph 1404. When the user interacts with the UI 1402 to move one slider (e.g., slider 1408) from one data point to a new data point, the UI can automatically update the display of the other slider (e.g., slider 1406) to the new data point.

FIG. 14 shows that the sliders are currently at FPR=0.420 and TPR=0.809. If the user moves slider 1406 to FPR=0.669, the UI can update the displayed position of slider 1408 to TPR=0.912. Likewise, if the user moves slider 1408 to TPR=0.564, the UI can update the displayed position of slider w1406 to FPR=0.141.

The user can select a data point, for example, by clicking on a button 1410. This action can cause the configuration unit 904 to use the decision thresholds contained in the data record corresponding to the selected data point to configure the component classifiers 802 that comprise the multi-classifier classification system 800.

Figure 15:
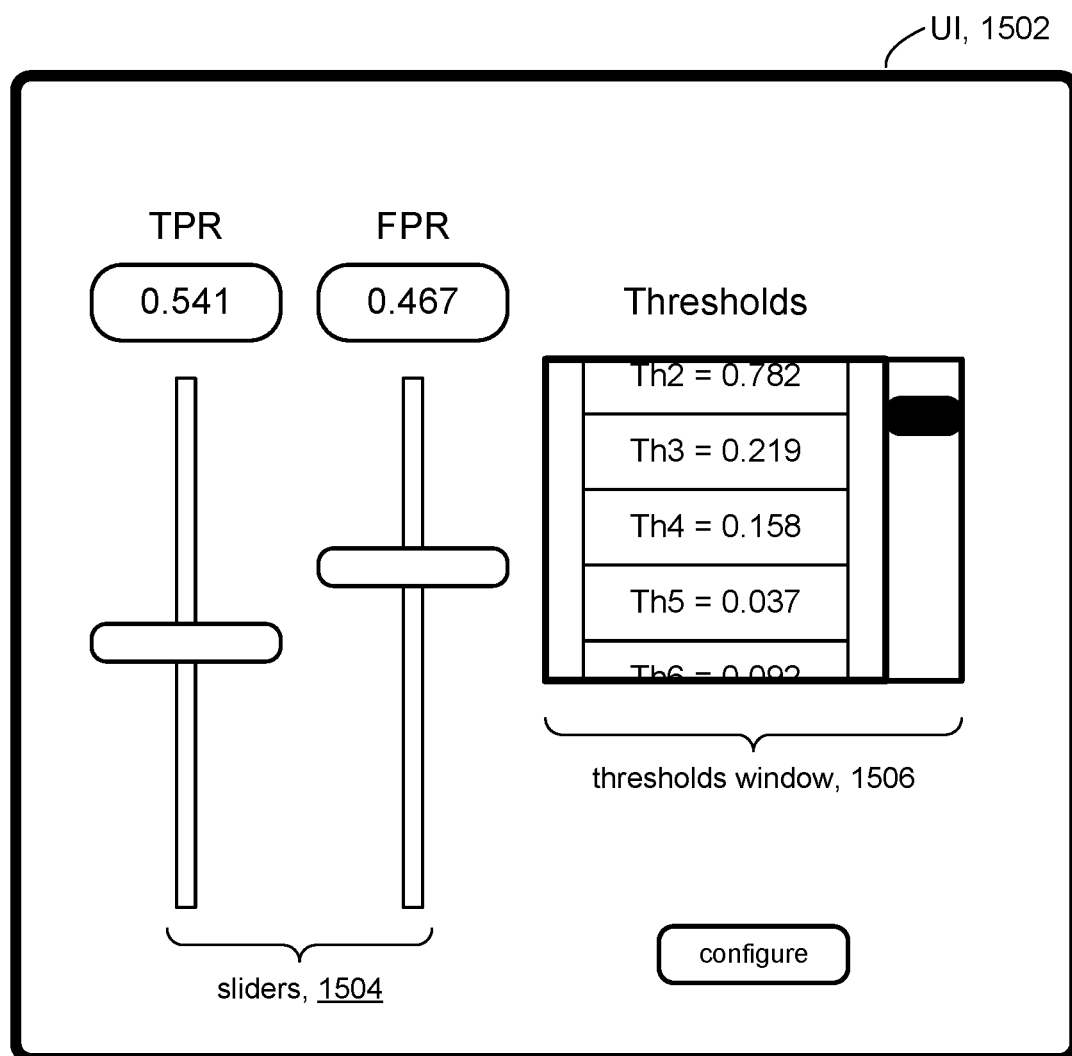

FIG. 15 illustrates an example of another user interface (UI) 1502 that the configuration unit 904 can display on display device 904a to present a representation of the performance data for multi-classifier classification system 800 in accordance with the present disclosure. Sliders 1504 can be presented to allow the user to select a system TPR or a system FPR. In some embodiments, UI 1502 can include a thresholds window 1506 that allows a user to view the decision thresholds contained in the data record corresponding the selected pair of TPR and FPR values, for example, via a scroll bar.

Figure 16:
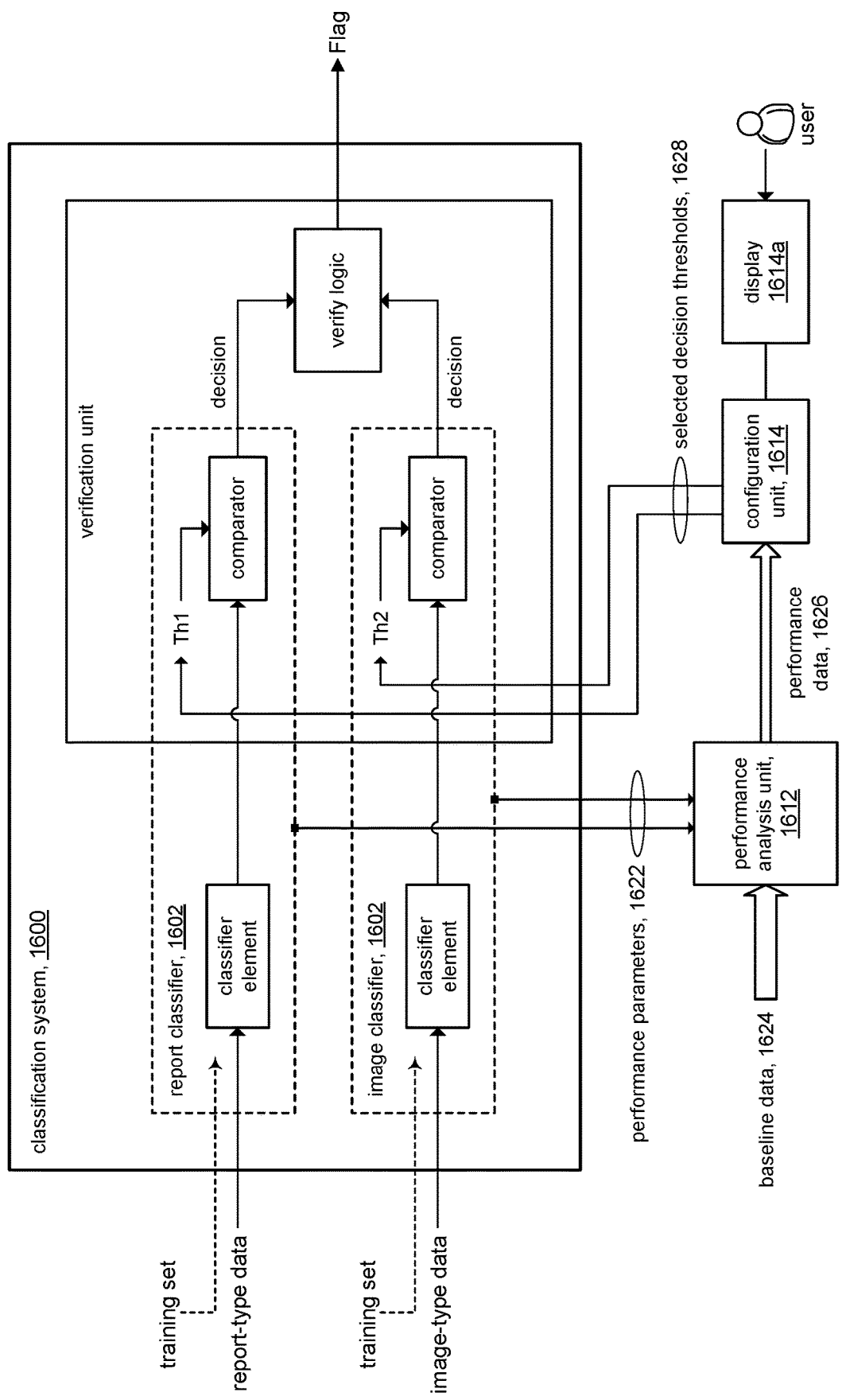
FIG. 16 shows a simple embodiment in accordance with the present disclosure used to explain performance analysis.

The discussion will now turn to a more detailed description of processing in the performance analysis unit 902 in FIG. 9 to generate performance data 916 in accordance with the present disclosure. As explained above, the performance data quantifies the overall performance of the multi-classifier classification system 800. In order to simplify the description of the various computations involved, a two-classifier configuration of the multi-classifier classification system 800 will be used without loss of generality of an n-classifier configuration, where n>2, such as shown in FIG. 16. In addition, the medical diagnosis example, and in particular the diagnosis of lung nodules, introduced above will be used as a specific example for the remaining discussion. Persons of ordinary skill can adapt the multi-classifier classification system 800 to other diagnostic applications in the medical field, to scientific and engineering applications, to economic analyses, to the social and behavioral sciences, and so on.

Referring now to FIG. 16, a two-classifier multi-classifier classification system 1600 for processing the diagnosis of lung nodules comprises two component classifiers 1602: a report classifier and an image classifier. The multi-classifier classification 1600 can verify medical diagnoses made by a professional (e.g., a doctor) using machine generated data.

A professional's diagnosis can be recorded in a report, such as a doctor's report, radiologist's report, or any other medical professional's report, notes, or similar electronic health records (EHR) about a patient. Such human-originated reports (to distinguish over machine-generated images) can be expressed in any form such as handwritten free-form text, text from one or more fields entered in an electronic form, or text corresponding to a selection in an electronic form, speech, and so on. Reports can be provided as report-type input data to the report classifier. The report classifier will output a TRUE decision if it determines from the input data that the report discusses a lung nodule, and will output a FALSE decision if the report classifier determines from the input data that the report does not discuss a lung nodule.

Machine-generated image data can include data generated or obtained, for example, from an electronic image, electronic test results, a video, X-Rays, ultrasounds (US), magnetic resonance (MM), Nuclear Medicine imaging, positron emission tomography (PET), computed tomography (CT scans), endoscopy (ES), mammograms (MG), digital radiography (DR), phosphor plate radiography, histopathology, or ophthalmology to name just a few examples. The machine generated data can be provided as image-type input data to the image classifier. The image classifier will output a TRUE decision if it detects a lung nodule in the image, and will output a FALSE decision if the image classifier does not detect a lung nodule in the image.

The multi-classifier classification 1600 uses the output decisions of the report classifier and the image classifier to predict whether the professional missed a lung nodule or did not miss a lung nodule. In other words, if the image classifier detects a lung nodule in a case image and the report classifier does not detect a lung nodule discussed in the corresponding case report, then the multi-classifier classification 1600 will indicate the professional missed a lung nodule. Otherwise, the multi-classifier classification 1600 will indicate that the professional did not miss a lung nodule. The system-level performance of multi-classifier classification 1600 refers to the accuracy of the predictions made by the multi-classifier classification.

There are three ways of quantifying the overall system performance of the multi-classifier classification 1600, referred to hereinafter as system 1600 or simply system:

Metric 1—ROC Curves

One metric of overall system performance is the ROC curve. We can calculate ROC curves for the system. There are mathematical formulas that allow us to convert the ROC curves of the individual component classifiers (e.g., report classifier, image classifier)v into the ROC curves of the system. An ROC curve is a collection of achievable TPR/FPR pairs for the system. The TPR tell us: if there is in fact a missed lung nodule in a case, what is the probability that the system will indicate that there is a miss? The FPR tells us: if there is not a missed lung nodule in a case, what is the probability that the system will (incorrectly) indicate that there is a miss?

Metric 2—Ratio of False Positives to True Positives

Another metric of overall system performance is the ratio of false positives to true positives. We can calculate the expected ratio of false positives to true positives for our system. A false positive occurs when there is no missed lung nodule in a case, but the system incorrectly indicates that there is a miss. A true positive occurs when there is a missed lung nodule, but the system correctly indicates that a miss occurred.

The ratio of false positives to true positives can therefore quantify how many system flags a doctor will need to look through before they find a true missed lung nodule.

In order to calculate this ratio, we need to use four quantities as input: the system TPR and FPR, the base rate of lung nodules in the population (i.e. the probability that a random case contains a lung nodule), and the miss rate for radiologists (i.e. the probability that a radiologist will miss a lung nodule in an image, if the image contains one). The system TPR and FPR can be calculated in the ROC curve. The lung nodule base rate and radiologist miss rate can be estimated using scientific literature on the topic. Given these four quantities, there is a mathematical formula that can be used to calculate the false positive/true positive ratio.

Metric 3—Improvement Ratio

We can calculate the improvement in the false positive/true positive ratio, over a baseline. For example, the baseline can be from a random inspection of cases by a doctor. For example, suppose that lung nodules occur in 3% of cases, and that radiologists catch 95% of lung nodules that occur. Given these assumptions, the probability of a missed lung nodule is 0.03*(1−0.95)=0.0015; i.e. 1 in 670 cases will contain a missed lung nodule. This means that, if doctors randomly sample cases in order to detect misses, then they will find a miss in 1 in 670 cases that they look at. Suppose for discussion purposes, the system achieves one true miss out of every 30 cases that it flags. Doctors using system would find one true miss for every 30 cases that they look at.

As a measure of the performance of our system, we can calculate the improvement in the system's ratio over the baseline. Given the assumptions above, the system gives a 1/30 true positive/false positive ratio, while the random baseline gives a 1/670 true positive/false positive ratio. Therefore, the system achieves a factor of (1/30)/(1/670)=22 improvement over the random baseline. That is, the system makes it 22 times more efficient to find missed lung nodules.

Computing Roc Curves

The discussion will now turn to a description for computing ROC curves in accordance with some embodiments. It is noted that the ROC curve can be used to compute the other two metrics (the expected ratio of true positives to false positives, and the improvement ratio).

To avoid confusion, we will be referring to the overall system (which aims to detect misses from image/report pairs) as a Workflow. We will refer to each component classifier (i.e. the report classifier, the image classifier, FIG. 16) as an App.

As a prerequisite for computing the Workflow ROC curve, we need two inputs:
1. The report-level App (report classifier) ROC curve
2. The image-level App (image classifier) ROC curve Each of these ROC curves is defined by a sequence of decision boundaries. A decision boundary has three components:
1. A classification decision threshold. For example, for the image classifier, an image will be classified as containing a lung nodule if the classifier emits a value which exceeds the decision (classifier) threshold Th2 (FIG. 16).
2. A false positive rate (FPR). This is the false positive rate for the classifier associated with the decision threshold.
3. A true positive rate (TPR). This is the true positive rate for the classifier associated with the decision (classifier) threshold.

The Workflow ROC curve is computed using these two ROC curves, namely the report-level App ROC curve and the image-level App ROC curve. There are three steps to compute the Workflow-level ROC curve from the two App ROC curves:

STEP 1. Take one image decision boundary and one report decision boundary. Compute the Workflow-level FPR for this pair of decision boundaries. Compute the Workflow-level TPR for this pair of decision boundaries.

STEP 2. Repeat step 1 for all pairs of image decision boundaries and report decision boundaries.

STEP 3. Find the pairs of image decision boundaries and report decision boundaries which form the Pareto frontier of Workflow performance.

Steps 1 and 3 require the most explanation. We will first consider how to compute the Workflow-level FPR in step 1 for a given image decision boundary and report decision boundary.

A. Workflow-Level FPR (Part 1, STEP 1)

We want to compute the Workflow-level (Workflow) FPR for the Workflow. A Workflow false positive occurs when two conditions hold:
1. The radiologist (or other professional), in fact, did not miss a nodule in the image.
2. The Workflow reports that the radiologist missed a nodule in the image.

In some embodiments, the performance analysis unit 1612 can include means for computing the Workflow FPR. The Workflow FPR can be expressed as the following conditional probability:

P(Workflow reports a missed nodule radiologist did not miss a nodule).

That is, we suppose that the radiologist did not miss a nodule, and we ask what is the probability that the Workflow reports a missed nodule.

We will use the following notation:
Workflow=True indicates that the Workflow reports a missed nodule,
Workflow=False indicates that the Workflow does not report a missed nodule,
Radiologist=True indicates that the radiologist has missed a nodule, and
Radiologist=False indicates that the radiologist has not missed a nodule.

The Workflow FPR can therefore be expressed as follows:
P(Workflow=True|Radiologist=False).
By the definition of conditional probability:

$$P(\text{Workflow} = \text{True} \mid \text{Radiologist} = \text{False}) = \frac{P(\text{Radiologist} = \text{False}, \text{Workflow} = \text{True})}{P(\text{Radiologist} = \text{False})}.$$

The complexity of computing the Workflow FPR comes from computing the joint probability P(Radiologist=False, Workflow=True). To compute this joint probability, we will introduce some additional notation:
Image=True if the image does in fact contain a nodule (and similarly for Image=False)
Report=True if the radiologist's report describes a nodule
Image Classifier=True if the image classifier App detects a nodule in the image
Report Classifier=True if the report classifier App detects a nodule being discussed in the radiology report.

The radiologist did not miss a nodule (i.e. Radiologist=False) if any of the following three conditions hold:
The image does not contain a nodule, and the report does not describe a nodule (Image=False, Report=False).
The image does not contain a nodule, and the report describes a nodule (Image=False, Report=True).
The image contains a nodule, and the report describes a nodule (Image=True, Report=True).

The only way that a false positive can occur is if the image classifier App detects a nodule in the image, and the report classifier App does not detect a nodule in the report (assuming that the system is not trying to estimate the number of nodules in the image, and only the presence/absence of one). The joint probability P(Radiologist=False, Workflow=True) therefore consists of a sum of the following three terms:
P(Image=False, Report=False, Workflow=True)=P (Image=False, Report=False, Image Classifier=True, Report Classifier=False), P(Image=False, Report=True, Workflow=True)=P(Image=False, Report=True, Image Classifier=True, Report Classifier=False), and P(Image=True, Report=True, Workflow=True)=P(Image=True, Report=True, Image Classifier=True, Report Classifier=False).

Some simplifying conditional independence assumptions can be made to allow decomposing these joint probabilities. The conditional independence assumptions are that:

P(Image Classifier|Image; Report)=P(Image Classifier|Image)

P(Report Classifier|Image; Report; Image Classifier)=P(Report Classifier|Report)

These conditional independence assumptions make a reasonable claim: the only factor that influences the image classifier is what appears in the image, and similarly the only factor that influences the report classifier is what appears in the report. The conditional independence assumptions allow for the following decompositions:

P(Image=False, Report=False, Image Classifier=True, Report Classifier=False)=P(Image=False)×P(Report=False|Image=False)×P(Image Classifier=True|Image=False)×P(Report Classifier=False|Report=False), P(Image=False, Report=True, Image Classifier=True, Report Classifier=False)=P(Image=False)×P(Report=True|Image=False)×P(Image Classifier=True|Image=False)×P(Report Classifier=False|Report=True), P(Image=True, Report=True, Image Classifier=True, Report Classifier=False)=P(Image=True)×P(Report=True|Image=True)×P(Image Classifier=True|Image=True)×P(Report Classifier=False|Report=True).

The sum of these three terms equals the joint probability P(Radiologist=False, Workflow=True). In order to compute the Workflow FPR, we need to divide this joint probability by the marginal probability P(Radiologist=False). This marginal probability equals the sum of three terms:

P(Radiologist=False)=P(Image=False, Report=False)+P(Image=False, Report=True)+P(Image=True, Report=True).

Each of these terms can be decomposed as the product of two probabilities, thus:

P(Image=False, Report=False)=P(Image=False)×P(Report=False|Image=False)

P(Image=False, Report=True)=P(Image=False)×P(Report=True|Image=False)

P(Image=True, Report=True)=P(Image=True)×P(Report=True|Image=False)

This completes the discussion of how to compute the Workflow FPR from the component decision boundaries.

To summarize, Workflow FPR can be expressed as a joint probability term divided by a marginal term:

$$P(\text{Workflow} = \text{True} \mid \text{Radiologist} = \text{False}) = \frac{P(\text{Radiologist} = \text{False}, \text{Workflow} = \text{True})}{P(\text{Radiologist} = \text{False})}.$$

In some embodiments in accordance with the present disclosure, the performance analysis unit 1612 (and in general 902, FIG. 9) can include means to compute the joint probability P(Radiologist=False, Workflow=True) as the sum of the following three terms:

P(Image=False)×P(Report=False|Image=False)×P(Image Classifier=True|Image=False)×P(Report Classifier=False|Report=False), P(Image=False)×P(Report=True|Image=False)×P(Image Classifier=True|Image=False)×P(Report Classifier=False|Report=True), P(Image=True)×P(Report=True|Image=True)×P(Image Classifier=True|Image=True)×P(Report Classifier=False|Report=True).

The performance analysis unit 1612 can further include means to compute the marginal probability P(Radiologist=False) as the sum of the following three terms:

P(Image=False)×P(Report=False|Image=False)

P(Image=False)×P(Report=False|Image=True)

P(Image=True)×P(Report=True|Image=False)

We finally note the information which is required in order to compute the above joint probability and marginal probability terms include baseline data 1624:

P(Image=True): a base rate of nodules occurring in images, where P(Image=False)=(1−P(Image=True)).

P(Report=True|Image=False): the probability that a radiologist will report that a nodule occurred in an image, when the image does not contain a nodule.

P(Report=True|Image=True): the probability that a radiologist will report that a nodule occurred in an image, when the image does contain a nodule.

and performance parameters 1622:

P(Image Classifier=True|Image=False): the FPR for the image classifier.

P(Image Classifier=True|Image=True): the TPR for the image classifier.

P(Report Classifier=True|Report=False): the FPR for the report classifier.

P(Report Classifier=True|Report=True): the TPR rate for the report classifier.

The baseline data 1624 can be obtained from external sources such as the technical literature on the topic, national or international statistics, empirical determinations, and the like.

In some embodiments, each component classifier 1602 can include means for determining its component TPR and component FPR performance parameters 1622. For example, computer system 710 can be configured to compute the component TPR and FPR. The FPR and TPR performance of the individual report and image classifiers can be quantified in a straightforward way, for a given report classifier decision threshold and an image classifier threshold. Using report and image training sets as respective input data to the report and image classifiers, we can calculate four quantities: the TPR and FPR of the report classifier, and the TPR and FPR of the image classifier. For example, the TPR of the report classifier can be computed as the number of TRUE decisions made by the classifier as a percentage of the number of reports in the training set that report the existence of a lung nodule. The FPR of the report classifier can be computed as the proportion of TRUE decisions made by the classifier as a percentage of the number of reports in the training set that do not report the existence of a lung nodule.

B. Workflow-Level TPR (Part 2, STEP 1)

In some embodiments, the performance analysis unit 1612 can include means for computing the Workflow-level (Workflow) TPR. We want to compute the Workflow TPR for a given image decision boundary and report decision boundary. A Workflow true positive occurs when two conditions hold:

The image contains a nodule, but the radiologist does not say this in the report.

The Workflow reports that the image contains a nodule, and that the report does not describe a nodule.

Using the notation above, the Workflow TPR is P(Workflow=True|Radiologist=True), namely the probability that the Workflow detects a missed nodule, given that the radiologist has missed a nodule. The Workflow TPR can be rewritten as:

P(Workflow=True|Radiologist=True)=P(Image Classifier=True, Report Classifier=False|Image=True, Report=False)

Given the same conditional independence assumptions that we used above, this can be written as:

P(Image Classifier=True, Report Classifier=False| Image=True, Report=False)=P(Image Classifier=True| Image=True)×P(Report Classifier=False|Report= False)

The term P(Image Classifier=True|Image=True) is the TPR for the image classifier. The term P(Report Classifier=False|Report=False) is equal to (1−FPR of the report classifier). Thus, the TPR for the image classifier App and the FPR for the report classifier are the only quantities we need to know in order to compute the Workflow TPR.

C. Pareto Frontier (STEP 3)

For every image decision boundary/report decision boundary pair, we computed the Workflow FPR and Workflow TPR using the formulas above. This gives us a very large collection of Workflow FPR and Workflow TPR values, and their associated image and report decision boundaries, collectively referred to as data records. In some embodiments, the performance analysis unit can include means for determining a subset of the resulting collection of data records.

Many of these image/report decision boundary pairs will be strictly dominated by other image/report decision boundary pairs. An image/report decision boundary pair A is strictly dominated by a different decision boundary pair B when B has a lower FPR and higher TPR than A. If A is strictly dominated by B, then there is no reason to ever choose A, as B is better at eliminating false positives and better at maximizing true positives. The Pareto frontier for our Workflow consists of the image/report decision boundary pairs that are not strictly dominated by any other image/report decision boundary pair. The image/report decision boundary pairs that are on the Pareto frontier form the ROC curve. The Pareto frontier can be efficiently computed in O(n log n) time.

This completes discussion of computing the ROC curve. The resulting Pareto frontier can be provided to the configuration unit 1614 as the sytem's performance data 1626. The discussion will now turn to calculating error bars for Workflow performance.

Calculating Error Bars for Workflow Performance

The above procedure for computing the Workflow ROC may not be exactly correct. Any errors in the App (component classifier) ROC curves for the image classifier or report classifier will lead to errors in the Workflow ROC. The goal here is to describe how we can bound the amount of probable error in the component ROC curves, and translate this into bounds on the amount of error in the Workflow ROC.

The App (component classifier) ROC curves are estimated from a finite sample of positive and negative examples. For example, suppose that there are 100 positive examples in the image classifier training set, and that the image classifier correctly labeled 95 of these as positive. This would lead to an estimated TPR of 0.95. This estimate may be incorrect: if the actual TPR is 0.94 (or some other nearby value), it could have easily classified 95 of the examples correctly.

A. Posterior Distribution Over Component Performance

Our first goal is therefore to quantify our uncertainty about the Component (App) ROC curves. An ROC curve consists of a sequence of (threshold, FPR, TPR) triples. For each threshold, we will calculate a distribution over the likely values of the FPR and TPR when the classifier uses this threshold.

We will explain how to calculate the FPR and TPR distributions for a particular component classifier. Let $n_{pos}$ be the number of positive examples in the training set, and let $n_{neg}$ be the number of negative examples. Let $n_{tp}$ be the number of correctly classified positive examples in the training set, and $n_{fp}$ be the number of incorrectly classified negative examples (both for a given setting of the threshold).

We use Beta (1,1) distributions to represent our prior beliefs about the FPR and TPR. After observing $n_{tp}$ correctly classified positive examples and $(n_{pos}-n_{tp})$ incorrectly classified positive examples, the posterior distribution over the TPR is a Beta $(1+n_{tp}, 1+n_{pos}-n_{tp})$ distribution. Similarly, after observing $n_{fp}$ incorrectly classified negative examples and $(n_{neg}-n_{fp})$ correctly classified negative examples, the posterior distribution over the FPR is a Beta $(1+n_{fp}, 1+n_{neg}-n_{fp})$ distribution.

B. Posterior Distribution Over Workflow Performance

The previous section describes how to calculate the exact posterior distribution over the TPR and FPR for a Component (App) classifier (and specific setting of the decision threshold). We will now describe how to combine component classifier distributions, in order to calculate a distribution over Workflow level performance.

We will compute a Monte Carlo estimate of the Workflow-level TPR and FPR distributions using the Component-level (App-level) distributions. Let $f_{workflow-tpr}$ be the function defined earlier in this document, which computes the Workflow TPR given the image classifier App TPR and report classifier App FPR. Similarly, let $f_{workflow-fpr}$ be the function which computes the Workflow FPR given the image classifier App TPR and FPR, and the report classifier App TPR and FPR.

Let $P_{image-tpr}$ be the probability distribution over TPR values for the image classifier, and similarly for $P_{image-fpr}$, $P_{report-tpr}$, and $P_{report-fpr}$. Then a single sample from the posterior distribution over Workflow FPR values can be constructed as follows:

First, take a sample from each of the four Component-level distributions:

$x_{image-tpr} \sim P_{image-tpr}$
$x_{image-fpr} \sim P_{image-fpr}$
$x_{report-tpr} \sim P_{report-tpr}$
$x_{report-fpr} \sim P_{report-fpr}$ Then, calculate the Workflow FPR value implied by these Component-level samples: $f_{workflow-fpr}(x_{image-tpr}; x_{image-fpr}; x_{report-tpr}; x_{report-fpr})$. This is a sample from the posterior distribution over Workflow FPR values, and a similar process can be used to take a sample from the posterior distribution over Workflow TPR values.

This process can be repeated n times, for a sufficiently large value of n (e.g. 1,000). These n samples will give us a discrete approximation of the posterior distribution over Workflow FPR values.

Error bars will consist of 95% credible intervals computed from these approximate posterior distributions. In order to compute the 95% credible interval from the distribution, we find a sample mower such that 2.5% of samples are below this sample, and a sample $x_{upper}$ such that 2.5% of samples are above this sample. The interval ($x_{lower}$; $x_{upper}$) contains approximately 95% of the probability mass from the posterior distribution.

Illustrative Implementation

The discussion will now turn to a description of an illustrative implementation of the foregoing operations. In some embodiments, the means for computing component TPRs and FPRs and the means for computing Workflow TPRs and FPRs can comprise software. In a particular implementation, for instance, the software was writing in Python version 3.5.

C. Inputs to the Software

The user of the package provides four inputs to the system:
1. An ROC curve for the image classifier.
2. An ROC curve for the report classifier.
3. P(Image=True): the base rate of nodules occurring in images.
4. P(Report=True|Image=True): the probability that the radiologist will report that a nodule occurred in an image, when the image does contain a nodule.

The ROC curve for each classifier can be represented as a .csv file, with three columns: the classification threshold, the corresponding false positive rate for the classifier, and the corresponding true positive rate for the classifier. Each row therefore contains a (classification threshold, FPR, TPR) triple. Each .csv file is placed in a specific directory by the user, and the software package will load these files from the directory.

The software package defines a Python Class, ComponentParameter, for representing the data from the .csv files. A ComponentParameter object contains the information from a single row of an ROC .csv file. It stores the classification boundary, FPR, and TPR for that row.

The software package creates one ComponentParameter object for each row in the image and report .csv files. We will use the term image-ComponentParameter object to refer to a ComponentParameter object for the image classifier, and similarly for the term report-ComponentParameter object.

D. Computing the Feasible Set

The "feasible set" consists of the set of achievable performance values by the overall system. The feasible set is computed by looping over all pairs of image-ComponentParameter objects and report-ComponentParameter objects. In other words, each pair consists of one image-ComponentParameter object and one report-ComponentParameter object. For example, if there are n rows in the image .csv file, and m rows in the report .csv file, then there are n×m pairs of ComponentParameter objects that are looped over.

For each pair of ComponentParameter objects that are looped over, the software package computes the system performance associated with that pair. This is done using the SystemParameter Class. A SystemParameter object takes as input four arguments:
1. An image-ComponentParameter object.
2. A report-ComponentParameter object.
3. P(Image=True): the base rate of nodules occurring in images.
4. P(Report=True j Image=True): the probability that the radiologist will report that a nodule occurred in an image, when the image does contain a nodule.

Using this information, it computes the system-level (Workflow) FPR and TPR associated with the pair of ComponentParameter objects. The procedure for doing this is described in the next sub-section.

1. Computing the System-Level FPR

The SystemParameter class computes the system-level FPR and TPR for each pair of ComponentParameter objects. The class defines two functions. The first function, compute_system_fp, takes four arguments:
1. An image-ComponentParameter object.
2. A report-ComponentParameter object.
3. P(Image=True)
4. P(Report=True|Image=True)

Using these arguments, the function computes the system-level (Workflow) FPR for the given pair of ComponentParameter objects in accordance with the operations described above.

2. Computing the System-Level TPR

The SystemParameter class defines a second function, compute_system_tp, which takes two arguments:
1. An image-ComponentParameter object.
2. A report-ComponentParameter object.

The function computes the system-level (Workflow) TPR for the pair of ComponentParameter objects in accordance with the operations described above.

Once the system-level FPR and TPR are computed, they are stored in the ComponentParameter object.

E. Computing the Pareto Frontier

In the previous section, the procedure for computing the feasible set was described. If there are n image-ComponentParameter objects, and m report-ComponentParameter objects, then the procedure returns n×m SystemParameter objects. Each of these SystemParameter objects contains the following information:
1. A pair of image classification thresholds and report classification thresholds.
2. A system-level FPR for this pair of thresholds.
3. A system-level TPR for this pair of thresholds.

The software package defines a function compute_Pareto_frontier, which computes the Pareto frontier for the feasible set. The function takes the feasible set, represented as a list of ComponentParameter objects, as its input. It lexicographically sorts the list according to two criteria:

Sort the ComponentParameter objects according to their FPR, from lowest to highest.

When multiple ComponentParameter objects share the same FPR, sort them according to their TPR, from highest to lowest.

Sorting the list has time complexity O(k log k), where k is the length of the list.

Using this sorted list, the Pareto frontier can be constructed in linear time. The function compute_Pareto_frontier does a single sweep through the sorted list. It initializes an empty list PF_list. Whenever a ComponentParameter object with a TPR greater than any observed so far is found, that ComponentParameter object is added to PF_list. After the sweep through the sorted list is complete, PF_list contains all ComponentParameter objects on the Pareto frontier. The function returns PF_HVlist.

F. Output from the Software

The function compute_Pareto_frontier computes the Pareto frontier for the system, which comprises the system-level ROC curve. After this ROC curve has been returned, the software package provide this curve for the user. In some embodiments, for example, the system-level ROC curve can be provided as performance data 1626 (e.g., in a .csv file) to the configuration unit 1614. The .csv file contains a single row (data record) for each point along the ROC curve. There are four columns in the file:

1. The image classification threshold
2. The report classification threshold
3. The system-level FPR for this pair of thresholds
4. The system-level TPR for this pair of thresholds The configuration unit 1614 can include means to for presenting the performance data 1626 to the user. In some embodiments, for example, the performance data 1626 can be presented in a UI such as illustrated in FIGS. 14 and 5, for instance, allowing the user to select a data record from the performance data. The configuration unit 1614 can include means for configuring the component classifiers with the decision thresholds 1628 in the selected data record. For example, the configuration unit 1614 can store each of the selected decision thresholds 1628 in a memory associated with the corresponding component classifier.

G. Summary

The software implementation can be summarized as follows:

Receive image ROC curves and report ROC curves as inputs. Receive base rates as inputs.

Loop over every pair of classification thresholds from the image and report ROC curves. For each pair, calculate the system-level FPR and TPR. Store each of these system-level performance values.

Compute the Pareto frontier for the set of system-level performance values found in the previous step.

Output the Pareto frontier to the user. This is the desired system-level ROC curve.

The above description illustrates various embodiments of the present disclosure along with examples of how aspects of the particular embodiments may be implemented. The above examples should not be deemed to be the only embodiments, and are presented to illustrate the flexibility and advantages of the particular embodiments as defined by the following claims. Based on the above disclosure and the following claims, other arrangements, embodiments, implementations and equivalents may be employed without departing from the scope of the present disclosure as defined by the claims.

What is claimed is:

1. A method in a system comprising a plurality of component classifiers, the method comprising:
    storing a plurality of data records that represent measures of performance of the system, each data record associated with a performance level of the system, each data record comprising:
        a plurality of decision thresholds for the plurality of component classifiers;
        a system true-positive rate (TPR) corresponding to the plurality of decision thresholds in said each data record; and
        a system false-positive rate (FPR) corresponding to the plurality of decision thresholds in said each data record,
        the performance level associated with said each data record being based on the system TPR and the system FPR;
    configuring the plurality of component classifiers comprising the system with the plurality of decision thresholds in a data record selected from among the plurality of data records based on the performance levels of the data records; and
    operating the system according to the configured plurality of component classifiers, wherein the system operates at a performance level that is approximated by the performance level associated with the selected data record.

2. The method of claim 1, further comprising presenting the plurality of data records to a user and receiving information from the user indicative of one of the plurality of data records as the selected data record.

3. The method of claim 1, wherein the plurality of data records is a subset of a plurality of candidate data records that is greater in number than the plurality of data records.

4. The method of claim 1, wherein the plurality of data records represents a Pareto frontier among a plurality of candidate data records that is greater in number than the plurality of data records.

5. The method of claim 1, wherein the system TPR and system FPR in a given data record characterizes the system when the plurality of component classifiers comprising the system are configured with the plurality of decision thresholds in the given data record.

6. The method of claim 5, wherein the system TPR and system FPR that characterize the system are determined by:
    presenting the plurality of component classifiers comprising the system with corresponding training data sets to determine component TPRs and FPRs of the component classifiers; and
    computing the system TPR and system FPR from the component TPRs and FPRs.

7. The method of claim 1, wherein each system FPR is based at least on a component TPR and a component FPR of a first component classifier comprising the system and on a component TPR and a component FPR of a second component classifier comprising the system.

8. The method of claim 7, wherein each system TPR is based on only the component TPR of a first component classifier comprising the system and on only the component FPR of a second component classifier comprising the system.

9. The method of claim 1, wherein the plurality of component classifiers includes an image classifier to classify machine-generated images and a report classifier to classify human-originated reports.

10. The method of claim 9, wherein the system FPR in a given data record is based on a TPR and an FPR of the image classifier configured with a first decision threshold among the plurality of decision thresholds in the given data record and a TPR and an FPR of the report classifier configured with a second decision threshold among the plurality of decision thresholds in the given data record.

11. The method of claim 10, wherein the system FPR is further based on base rates that are independent of performance of the image classifier and performance of the report classifier.

12. A system comprising a plurality of component classifiers and means for configuring the plurality of component classifiers comprising:
    means for storing a plurality of data records that represent measures of performance of the system, each data record associated with a performance level of the system, each data record comprising:
        a plurality of decision thresholds for the plurality of component classifiers;
        a system true-positive rate (TPR) corresponding to the plurality of decision thresholds in said each data record; and
        a system false-positive rate (FPR) corresponding to the plurality of decision thresholds in said each data record,
        the performance level associated with said each data record being based on the system TPR and the system FPR; and means for configuring the plurality of component classifiers comprising the system with the plurality of decision thresholds in a data record selected from among the plurality of data records based on the performance levels of the data records, wherein when operating the system according to the configured plurality of component classifiers, the system operates at a performance level that is approximated by the performance level associated with the selected data record.

13. The system of claim 12, further comprising means for presenting the plurality of data records to a user and receiving information from the user indicative of one of the plurality of data records as the selected data record.

14. The system of claim 12, wherein the plurality of data records is a subset of a plurality of candidate data records that is greater in number than the plurality of data records.

15. The system of claim 12, wherein the plurality of data records represents a Pareto frontier among a plurality of candidate data records that is greater in number than the plurality of data records.

16. The system of claim 12, wherein the system TPR and system FPR in a given data record characterizes the system when the plurality of component classifiers comprising the system are configured with the plurality of decision thresholds in the given data record.

17. The system of claim 16, wherein the system TPR and system FPR that characterize the system are determined by:
presenting the plurality of component classifiers comprising the system with corresponding training data sets to determine component TPRs and FPRs of the component classifiers; and
computing the system TPR and system FPR from the component TPRs and FPRs.

18. A non-transitory computer-readable storage medium in a system comprising a plurality of component classifiers, the non-transitory computer-readable storage medium having stored thereon computer executable instructions, which when executed by a computer device, cause the computer device to:
store a plurality of data records that represent measures of performance of the system, each data record associated with a performance level of the system, each data record comprising:
a plurality of decision thresholds for the plurality of component classifiers;
a system true-positive rate (TPR) corresponding to the plurality of decision thresholds in said each data record; and
a system false-positive rate (FPR) corresponding to the plurality of decision thresholds in said each data record,
the performance level associated with said each data record being based on the system TPR and the system FPR;
configure the plurality of component classifiers comprising the system with the plurality of decision thresholds in a data record selected from among the plurality of data records based on the performance levels of the data records; and
operate the system according to the configured plurality of component classifiers, wherein the system operates at a performance level that is approximated by the performance level associated with the selected data record.

19. The non-transitory computer-readable storage medium of claim 18, wherein the computer executable instructions, which when executed by the computer device, further cause the computer device to present the plurality of data records to a user and receiving information from the user indicative of one of the plurality of data records as the selected data record.

20. The non-transitory computer-readable storage medium of claim 18, wherein the plurality of data records is a subset of a plurality of candidate data records that is greater in number than the plurality of data records.

21. The non-transitory computer-readable storage medium of claim 18, wherein the plurality of data records represents a Pareto frontier among a plurality of candidate data records that is greater in number than the plurality of data records.

22. The non-transitory computer-readable storage medium of claim 18, wherein the system TPR and system FPR in a given data record characterizes the system when the plurality of component classifiers comprising the system are configured with the plurality of decision thresholds in the given data record.

23. An apparatus in a system comprising a plurality of component classifiers, the apparatus comprising:
one or more computer processors; and
a computer-readable storage medium comprising instructions for controlling the one or more computer processors to be operable to:
store a plurality of data records that represent measures of performance of the system, each data record associated with a performance level of the system, each data record comprising:
a plurality of decision thresholds for the plurality of component classifiers;
a system true-positive rate (TPR) corresponding to the plurality of decision thresholds in said each data record; and
a system false-positive rate (FPR) corresponding to the plurality of decision thresholds in said each data record,
the performance level associated with said each data record being based on the system TPR and the system FPR;
configure the plurality of component classifiers comprising the system with the plurality of decision thresholds in a data record selected from among the plurality of data records based on the performance levels of the data records; and
operate the system according to the configured plurality of component classifiers, wherein the system operates at a performance level that is approximated by the performance level associated with the selected data record.

24. The apparatus of claim 23, wherein the computer-readable storage medium further comprises instructions for controlling the one or more computer processors to be operable to present the plurality of data records to a user and receiving information from the user indicative of one of the plurality of data records as the selected data record.

25. The apparatus of claim 23, wherein the plurality of data records is a subset of a plurality of candidate data records that is greater in number than the plurality of data records.

26. The apparatus of claim 23, wherein the plurality of data records represents a Pareto frontier among a plurality of candidate data records that is greater in number than the plurality of data records.

27. The apparatus of claim 23, wherein the system TPR and system FPR in a given data record characterizes the system when the plurality of component classifiers comprising the system are configured with the plurality of decision thresholds in the given data record.

* * * * *